US006772006B2

(12) United States Patent
Piraino et al.

(10) Patent No.: US 6,772,006 B2
(45) Date of Patent: Aug. 3, 2004

(54) METHOD AND DEVICE FOR CONTROLLING PEAK CURRENTS IN A MEDICAL DEVICE

(75) Inventors: Daniel W. Piraino, Seattle, WA (US); D. Craig Edwards, Fall City, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 430 days.

(21) Appl. No.: 09/923,780

(22) Filed: Aug. 6, 2001

(65) Prior Publication Data

US 2003/0028220 A1 Feb. 6, 2003

(51) Int. Cl.$^7$ .................................................. A61N 1/39
(52) U.S. Cl. .............................................. 607/7; 607/6
(58) Field of Search ........................... 607/4–8; 600/547

(56) References Cited

U.S. PATENT DOCUMENTS

| 4,574,810 | A | * | 3/1986 | Lerman ........................... 607/8 |
| 5,433,732 | A | | 7/1995 | Hirschberg et al. |
| 5,769,872 | A | | 6/1998 | Lopin et al. |
| 6,148,233 | A | * | 11/2000 | Owen et al. .................... 607/5 |
| 6,241,751 | B1 | * | 6/2001 | Morgan et al. ................. 607/8 |

FOREIGN PATENT DOCUMENTS

EP 0 569609 A1 11/1993

OTHER PUBLICATIONS

Bardy, G.H., et al. "Multicenter Comparison of Truncated Biphasic Shocks and Standard Damped Sine Wave Monophasic Shocks for Transthoracic Ventricular Defibrillation," *Circulation* 94(10):2507–2514, 1996.
Gliner, B.E., and R.D. White, "Electrocardiographic Evaluation of Defibrillation Shocks Delivered to Out–of–Hospital Sudden Cardiac Arrest Patients," *Resuscitation 41*:133–144, 1999.
Mittal, S., et al. "Comparison of a Novel Rectilinear Biphasic Waveform With a Damped Sine Wave Monophasic Waveform for Transthoracic Ventricular Defibrillation," *Journal of the American College of Cardiology 34*(5):1595–1601, 1999.
Mittal, S., et al. "Transthoracic Cardioversion of Atrial Fibrillation; Comparison of Rectilinear Biphasic Versus Damped Sine Wave Monophasic Shocks," *Circulation 101*: 1282–1287, Mar. 21, 2000.
European Search Report, Nov. 26, 2003.

* cited by examiner

*Primary Examiner*—Kennedy Schaetzle
*Assistant Examiner*—Kristen Droesch
(74) *Attorney, Agent, or Firm*—Ingrassia Fisher & Lorenz, P.C.

(57) ABSTRACT

In one embodiment, a method is characterized by measuring a patient parameter associated with a human body; in response to the patient parameter, retrieving a maximum expected device parameter; and setting a limit on an energy source such that during defibrillation of the patient a defibrillation parameter associated with the maximum expected device parameter is within a defined tolerance. In another embodiment, a method is characterized by specifying at least one device parameter limit of a defibrillation unit; and in response to the at least one specified device parameter, determining a prediction confidence level at which the device parameter limit is exceeded for one or more values of a patient parameter. In another embodiment, a method is characterized by specifying a prediction confidence level to which a defibrillation unit device parameter is correlated with one or more values of a patient parameter; and in response to the specified prediction confidence level, determining a defibrillation unit device parameter from one or more values of a patient parameter. In other embodiments, circuitry is used to at least partially effect the foregoing-described methods; the circuitry can include and/or utilize virtually any combination of hardware, software, and/or firmware configured to effect the foregoing-described method, depending upon the design choices of the system designer. In other embodiments, signal bearing media at least partially bear the foregoing-described methods.

34 Claims, 19 Drawing Sheets

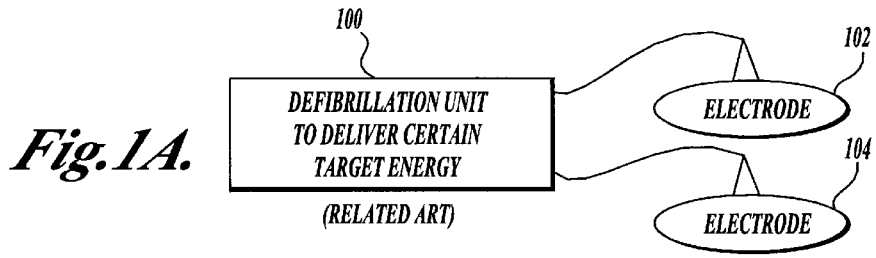
*Fig.1A.*
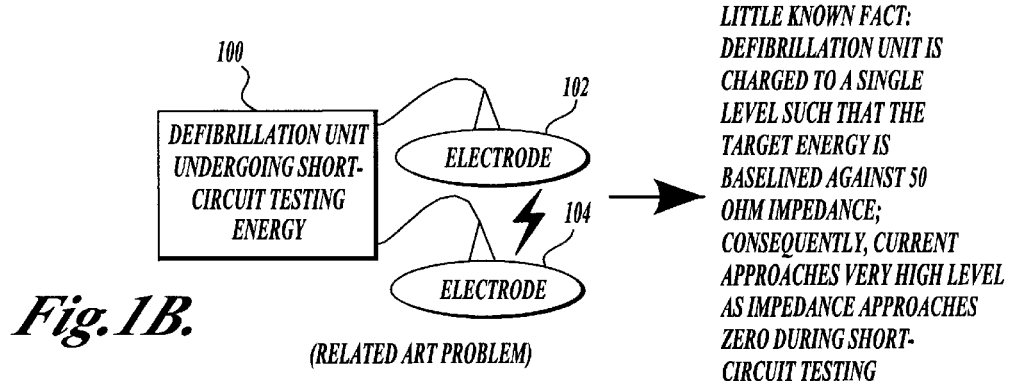
*Fig.1B.*
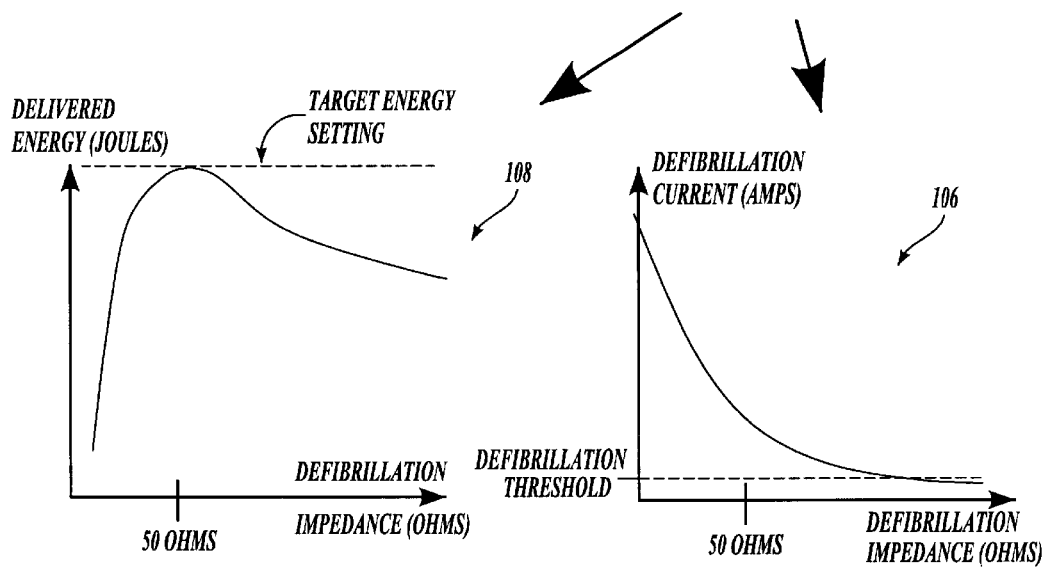
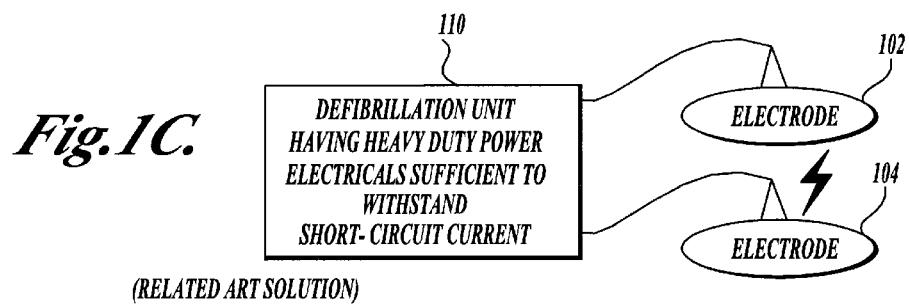
*Fig.1C.*

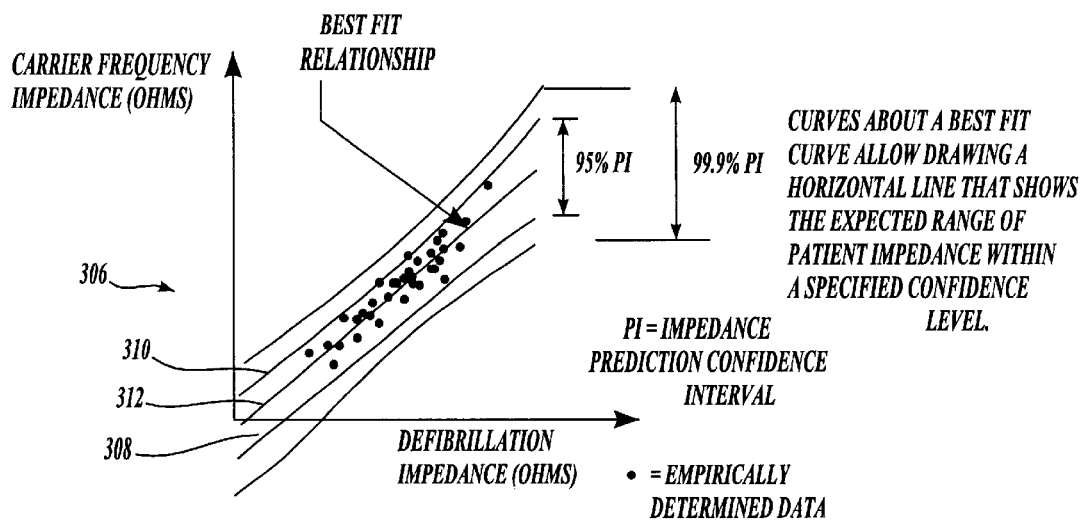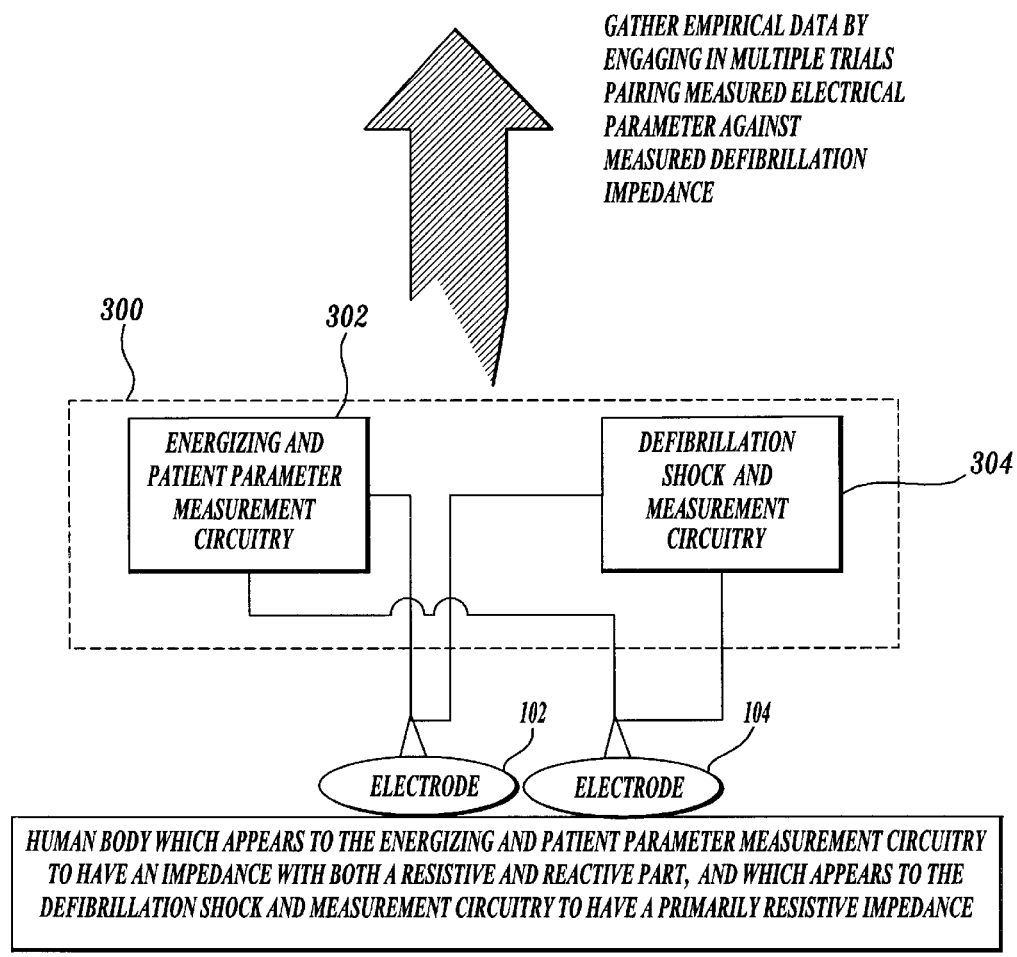
Fig.3A.

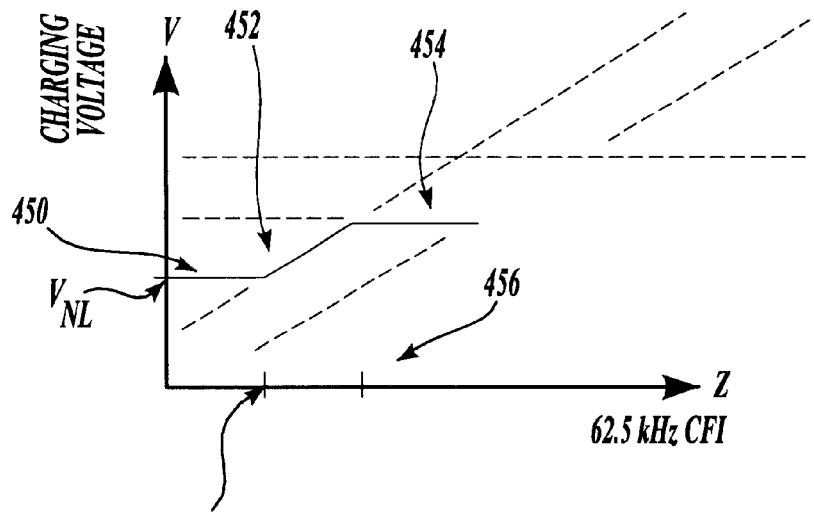

CFI ASSOCIATED WITH A
MINIMUM DEFIBRILLATION
IMPEDANCE OF ZERO.
CONSEQUENTLY CHARGING
TO $V_{NL}$ WILL PROTECT
ELECTRICAL COMPONENTS IF
$V_{NL} = Z_{INT} I_{MAX}$, WHERE
$Z_{INT}$ IS THE INTERNAL
IMPEDANCE OF THE DEVICE
(5Ω FOR EXAMPLE) AND
$I_{MAX}$ IS THE MAXIMUM
ALLOWED VALUE FOR AN
ELECTRICAL PARAMETER
(E.G., CURRENT).

CFI ASSOCIATED WITH A
DEFIBRILLATION IMPEDANCE
AT WHICH ELECTRICAL
COMPONENTS MAY BE DAMAGED
AT LOWER CFI'S UNLESS
CHARGING VOLTAGE IS
REDUCED.

VOLTAGE COMPENSATION

*Fig. 4B.*

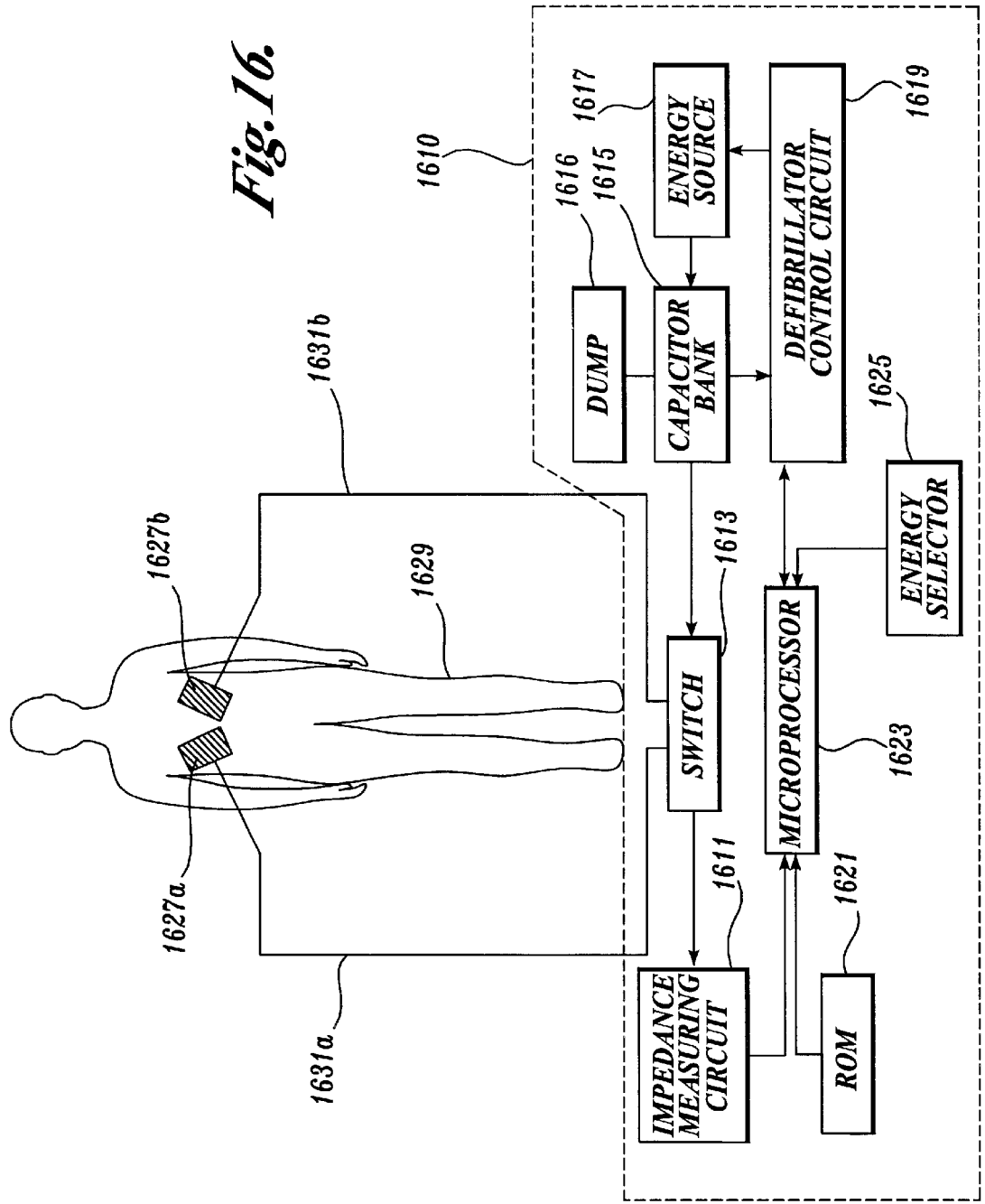

METHOD AND DEVICE FOR CONTROLLING PEAK CURRENTS IN A MEDICAL DEVICE

FIELD OF THE INVENTION

The present invention relates, in general, to defibrillation units.

BACKGROUND OF THE INVENTION

Defibrillation units have been widely used to administer one or more high-voltage, direct-current shock pulses to a patient experiencing cardiac arrest occurring because of asynchronous depolarization, i.e., fibrillation, of cardiac cells. Unconsciousness and/or death generally follow quickly after cardiac arrest. When sufficient electrical energy is delivered to the heart from a defibrillator through two or more electrodes positioned to engage the patient, fibrillation of the cardiac cells may be arrested. Thereafter, synchronous or normal depolarization of the cardiac cells will often resume.

There are two basic types of defibrillation units known in the art: external defibrillation units (which generally administer energy to a heart via electrodes placed in proximity to the surface of a patient's body or via electrodes placed on the surface of a heart exposed during open-heart surgery) and internal defibrillation units (which generally administer energy to a heart by electrodes inserted via incisions in a patient's body and subsequent placement of the electrodes either directly in or in extremely close proximity to the patient's heart.)

With reference now to FIG. 1A, shown is a pictographic representation of related-art external defibrillation unit 100. Depicted are external electrodes 102, 104 which are typically positioned on a patient's chest in the case of external defibrillation in order to deliver defibrillation energy.

External defibrillation units (e.g., external defibrillation unit 100) are often used in chaotic and stressful environments. For example, field use of defibrillators is quite common in which paramedics rush to a scene of a person who has experienced cardiac arrest. In these cases the probability for accidental misuse can be high and it is not uncommon for the external electrodes (e.g., external electrodes 102 and 104) to come in contact with each other when the defibrillation unit is on and fully charged (defibrillators often store and discharge energy via the use of storage capacitors—devices which condense and store electrical energy), which effectively amounts to an electrical short circuit between the external defibrillation electrodes.

In addition, there are reports of intentional misuse by those experimenting with units who do not understand the implications of such activity and who purposely bring the electrodes in contact with each other and discharge the defibrillator.

The possibility of accidental or purposeful short circuiting of electrodes has been recognized by various regulatory agencies. As a result of such recognition, various regulatory agencies have instituted what is know as "short-circuit testing," which typically requires that an external defibrillation unit (e.g., external defibrillation unit 100) be able to withstand a certain number (e.g., ten (10)) of short-circuit discharges from a fully-charged state, where the required number of short-circuit discharges are done in rapid succession.

Referring now to FIG. 1B, shown is a pictographic representation of defibrillation unit 100 undergoing short-circuit testing in the context of two graphs 106, 108. Depicted is the little-known fact that the energy which defibrillation unit 100 is set to deliver (such setting done either internally or via controls external to defibrillation unit 100) is actually calibrated (or baselined) against an expected 50 ohm "defibrillation impedance" (defibrillation impedance is a measure of how much the patient itself will impede the delivery of defibrillation energy when viewed at or near the standpoint of the source delivering the defibrillation energy.) As in the case of short-circuit testing, the amount of delivered energy to be used in dosing protocols is specified by defibrillation industry standards. For example, the American Heart Association recommends that in adults an energy level of 200 joules be set for the first defibrillation pulse, 200 or 300 joules for a second defibrillation pulse (if the first is unsuccessful), and 360 joules for a third defibrillation pulse (if the second pulse is unsuccessful)—all of such pulses generally baselined or calibrated for discharge through a 50-ohm defibrillation impedance.

Illustrated on graph 106 of FIG. 1B is the fact that if the energy is baselined against 50 ohms of defibrillation impedance (i.e., the unit is charged to a voltage which will deliver the specified energy into 50 ohms, e.g., graph 108), then extremely high levels of current will result within defibrillation unit 100 when defibrillation unit 100 undergoes short-circuit testing. These high levels of current are far in excess of that needed to defibrillate. The extremely high levels of current cause great strain on the electrical components of defibrillation unit 100, and can cause failure of such components. However, given the fact that approval of various regulatory agencies is extremely important in the commercial marketplace, and that such failures would be intolerable to customers, most makers of defibrillation units (e.g., defibrillation unit 100) have generated a solution to the problems associated with the extremely high current discharges and associated electrical component stresses depicted and described in relation to FIG. 1B.

With reference now to FIG. 1C, shown is a related-art solution to the problems depicted and described in relation to FIG. 1B. Insofar as the required defibrillation energy is fixed by standards, defibrillation unit makers have had little choice in adjusting the amount of energy to be delivered into a 50 ohm impedance. Accordingly, what is commonly done in the art is to create a defibrillation unit 110, which is essentially defibrillation unit 100 modified to have high-current electrical components sufficient to withstand the extremely high short-circuit testing discharges depicted and described in relation to graph 106 of FIG. 1B.

The inventors named herein (hereinafter, inventors) have recognized that the related-art solution of FIG. 1C works well, but that such solution does have some significant associated problems. One such problem is that the high-current electrical components necessary to allow defibrillation unit 110 to pass the regulatory-agency-required short-circuit testing are expensive and difficult to obtain. Another is that permitting such high currents to flow can cause failure of such electrical components. However, the inventors have also recognized that the related art solution depicted in FIG. 1C is still the most commonly used because those in the related art have not yet discerned a way to consistently meet the regulatory-agency-required short-circuit testing and simultaneously meet the various industry standards related to the required amounts of defibrillation energy.

SUMMARY OF THE INVENTION

The present invention allows defibrillation units to consistently meet regulatory-agency-required short-circuit testing while simultaneously meeting various industry-standards related to required amounts of defibrillation energy (e.g., 360 Joules) in such a way that the unnecessarily high current electrical components of the related art are no longer necessary.

In one embodiment, a method is characterized by measuring a patient parameter associated with a human body; in response to the patient parameter, retrieving a maximum expected device parameter; and setting a limit on an energy source such that during defibrillation of the patient a defibrillation parameter associated with the maximum expected device parameter is within a defined tolerance.

In another embodiment, a method is characterized by specifying at least one device parameter limit of a defibrillation unit; and in response to the at least one specified device parameter, determining a prediction confidence level at which the device parameter limit is exceeded for one or more values of a patient parameter.

In another embodiment, a method is characterized by specifying a prediction confidence level to which a defibrillation unit device parameter is correlated with one or more values of a patient parameter; and in response to the specified prediction confidence level, determining a defibrillation unit device parameter from one or more values of a patient parameter.

In other embodiments, circuitry is used to at least partially effect the foregoing-described methods; the circuitry can include and/or utilize virtually any combination of hardware, software, and/or firmware configured to effect the foregoing-described method, depending upon the design choices of the system designer. In other embodiments, signal bearing media at least partially bear the foregoing-described methods.

The foregoing is a summary and thus contains, by necessity, simplifications, generalizations and omissions of detail; consequently, those skilled in the art will appreciate that the summary is illustrative only and is not intended to be in any way limiting. Other aspects, inventive features, and advantages of this patent application will become apparent in the non-limiting detailed description set forth below.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A shows a pictographic representation of related-art external defibrillation unit 100.

FIG. 1B shows a pictographic representation of defibrillation unit 100 undergoing short-circuit testing in the context of two graphs 106, 108.

FIG. 1C shows a related-art solution to the problems depicted and described in relation to FIG. 1B.

FIG. 3A shows an example of one way in which families of curves, such as curves 208, 210 depicted in graph 202, can be constructed.

FIG. 4B shows one implementation whereby voltage can be adjusted in response to a measured carrier frequency impedance.

FIG. 16 depicts a pictorial representation of a processor-based system with which illustrative embodiments of the devices and/or processes described herein may be implemented via virtually any combination of software, hardware, and firmware with only minimal experimentation by those having ordinary skill in the art.

As used herein, similar reference numerals in different figures denote similar components.

DETAILED DESCRIPTION OF THE PREFERRED EMBODIMENT

As was noted in the background section above, the related-art solution to the requirement that defibrillation units pass regulatory-agency-required short-circuit testing is to introduce into defibrillation units high-power electrical components sufficient to stand the stress that results from the short-circuit testing. The inventors have discovered a way to construct defibrillation units which supply industry-required levels of defibrillation energy and which will survive the short circuit testing described in the background section above, but which can do the foregoing via the use of much-lower-power components than commonly utilized in the related art. That is, the inventors' solution provides performance substantially comparable to related-art defibrillation units, but does so in a way in which defibrillation units can be constructed from much cheaper components than those utilized in the related-art defibrillation units. In addition, the techniques described herein will stress electrical components much less than that generally required in the related art, which will generally lead to higher reliability of such components. Although maximum-rated electrical current will be described herein for sake of illustration, those having ordinary skill in the art will recognize that electrical components often have absolute maximum ratings for several parameters, such as power, current, and voltage; accordingly, although the present discussion describes current as the parameter of interest, those having ordinary skill in the art will recognize that such discussion can be generalized to other like parameters without undue experimentation. Accordingly, it will be appreciated that the present invention may be applied to any defibrillation unit components associated with such parameters, such components only depending on the particular circuit topology of the unit. For example, in a typical biphasic defibrillator, such components may include the electrical components of an H-Bridge discharge circuit, e.g., silicon controlled rectifiers and/or insulated gate bipolar transistors, and their respective connectors and wires.

Figure 2:
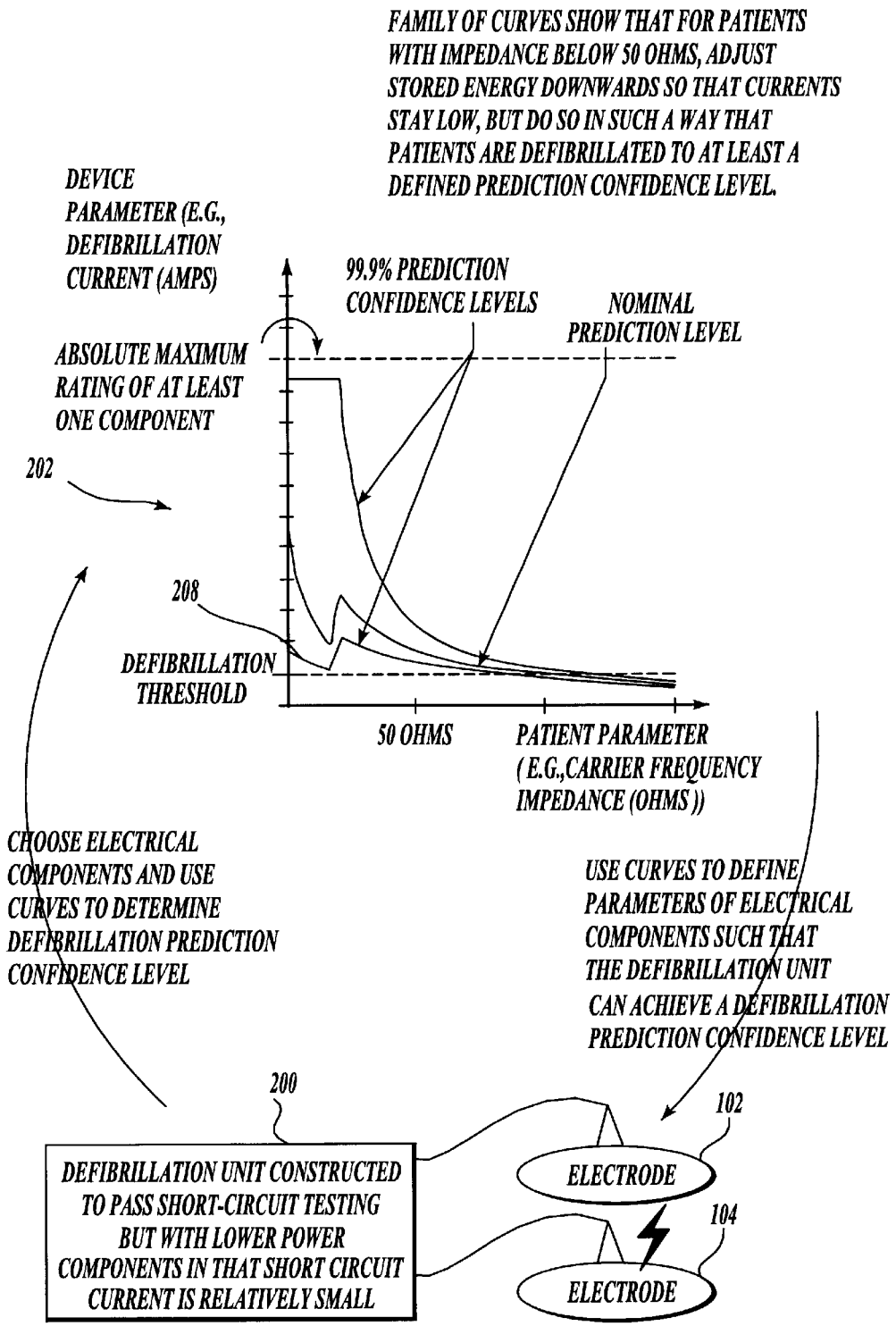
FIG. 2 shows a design process which the inventors have devised which provide the foregoing referenced benefits, as well as other benefits which will be apparent to those having ordinary skill in the art.

Referring now to FIG. 2, shown is a design process which the inventors have devised which provides the foregoing-referenced benefits, as well as other benefits which will be apparent to those having ordinary skill in the art. As illustrated in FIG. 2, the inventors' solution makes use of an "iterative" design strategy which gives great flexibility to defibrillation unit system designers. As shown in FIG. 2, utilizing the inventors' scheme, a defibrillation unit designer can specify certain types of electrical components which the designer would prefer to use in defibrillation unit 200. Subsequent to said specification, the system designer may use the defined tolerances of the electrical components specified (those having ordinary skill in the art will recognize that most electrical components have defined operating characteristics where their performance is substantially guaranteed) to determine the absolute upper limit of some device parameter (e.g., electrical current) at which defibrillation unit 200 can be expected to reliably operate.

As illustrated in FIG. 2, this component-specified operating limit (i.e., the upper limit on some electrical parameter, such as current) can be used with a family of curves, such as those shown on graph 202, to determine an impedance at which it can be said with a percentage confidence that substantially all of patients encountered will be successfully defibrillated utilizing the defined electrical components of defibrillation unit 200. (How graph 202 is constructed is explained subsequently in relation to FIG. 3A; however, at present, it is most clear to discuss how graph 202 is used in the design cycle. In addition, while graph 202 of FIG. 2 shows that the design parameter of interest is defibrillation current, it is to be understood that the "iterative" design strategy employed herein could be utilized for other design parameters, such as voltage, or time. However, as an example, defibrillation current is discussed herein as the design parameter of interest.)

Continuing to refer to FIG. 2, once the upper-end limit defined by the specified electrical components of defibrillation unit 200 has been determined from the family of curves shown on graph 202, a determination can be made as to the confidence that patients will be defibrillated by a defibrillation unit having the specified electrical components (assuming the defibrillation unit is operating within tolerance). To see how this is done, note that curves 208, 210 shown in graph 202 have associated defibrillation prediction confidence levels referenced against various values of a certain patient parameter (e.g., Carrier Frequency Impedance (CFI)). If the lower curve 208 is above the defibrillation threshold, then it can be determined that patients will be defibrillated at least to the confidence prediction level of the curves 208, 210. For example, if the curves 208, 210 represent the 99.9% prediction confidence levels, and if the lower curve is above the defibrillation threshold, then it can be determined with more than 99.9% confidence that patients will be defibrillated by a unit having the specified electrical components.

From a design standpoint, in the event that the defibrillation prediction confidence level which can be generated with the chosen electrical components for defibrillation unit 200 is not substantially optimal (e.g., the behavior is substantially optimal when the region defined and/or bracketed by curves 208, 210 is above the defibrillation threshold), then family of curves 208, 210 of graph 202, can be used to determine the substantially minimum device parameter (e.g., current) characteristics necessary to also insure that the patients will be defibrillated to the specified confidence level. Accordingly, thereafter the system designer can utilize such defined device parameter characteristics to select a new set of electrical components for defibrillation unit 200, such that the defibrillation unit 200 is substantially ensured to defibrillate at the desired defibrillation prediction confidence level at a lower (or lowest) cost of electrical components, at least insofar as the device parameter characteristic or characteristics of interest are concerned.

As was just shown and described in relation to FIG. 2, note that the inventors' "iterative" design scheme allows great flexibility in the design of defibrillation units in that a system designer can (1) specify the electrical components the system designer desires to use, (2) determine if such specified electrical components will give acceptable prediction confidence levels with respect to patients to be defibrillated, and, if not, (3) thereafter utilize a family of curves such as those illustrated in graph 202 to determine adjustments necessary to the system-designer-chosen components such that the defibrillation threshold is exceeded to a prediction confidence level deemed adequate. Notice that it will not necessarily always be true that the system designer will have to choose electrical components with increased ratings; that is, in some instances the system designer may determine that the chosen electrical components exceed the defibrillation threshold to a greater prediction confidence level than the system designer deems necessary, in which case the system designer can specify electrical components with progressively lower ratings (e.g., absolute maximum current ratings) and engage in the iterative process shown in FIG. 2 while the electrical components of the defibrillation unit 200 have ratings in excess of the defibrillation threshold to a prediction confidence level specified by the system designer.

Continuing to refer to FIG. 2, notice that in the alternative to the procedure just outlined, the system designer could begin by examining curves 208, 210 of graph 202 and via the use of such curves substantially immediately determine the minimum expected device parameters (e.g., electrical characteristics) of the components of defibrillation unit 200 which will give a desired defibrillation prediction confidence level related to patients likely to be successfully defibrillated with defibrillation unit 200. Hence, the inventors' scheme of defibrillation design illustrated in FIG. 2 gives great flexibility in the design of defibrillation units in that it allows a designer to either (a) begin with a set of electrical components and engage in iterative computational/analytical design to rapidly reach acceptable electrical component specification, or (b) begin with a specified prediction confidence level of successful defibrillation and use the defibrillation prediction confidence level of given curves (e.g., current 208, 210), to define the substantially optimal device parameters related to the electrical components of defibrillation unit 200.

While the iterative design scheme has been described in the context of a system designer choosing components and/or examining families of curves, those skilled in the art will recognize that the iterative design process described herein could be readily implemented without undue experimentation via virtually any combination of hardware, software, and/or firmware via standard engineering practices well known to those in the art.

Notice that the inventors' iterative design scheme described herein completely reverses that utilized in the related art. That is, rather than defining certain levels of energy to be delivered to a prespecified load, and then "beefing up" the electrical components of a defibrillation unit to withstand a short-circuit, the inventors' scheme allows either (a) the electrical components or (b) a defibrillation prediction confidence level to be specified first, and such electrical components or defibrillation prediction confidence level to be thereafter utilized with the iterative scheme in order to determine the electrical components desired/necessary. Thus, the inventors' scheme inverts the method of the related art and hence, represents a significant advance in the design of defibrillation units.

With reference now to FIG. 3A, shown is an example of one way in which a family of curves, such as curves 208, 210 depicted in graph 202, can be constructed. As noted above, the desired amount of energy to be delivered to patients in order to successfully defibrillate patients has been specified by various regulatory agencies, and this energy relationship is used to define the curves shown in graph 202 of FIG. 2. As shown and discussed in relation to FIG. 2, the family of curves of graph 202 has associated with them defibrillation prediction confidence levels. These defibrillation prediction confidence levels are empirically generated via use of the process shown and described in FIG. 3A.

Shown in FIG. 3A is defibrillation unit 300. Depicted internal to defibrillation unit 300 are energizing and patient parameter measurement circuitry 302 and defibrillation shock and measurement circuitry 304, both of which are electrically connected with electrodes 102 and 104 via engineering techniques well known to those having ordinary skill in the art. Illustrated is that electrodes 102 and 104 are in contact with a human body which appears to the energizing and patient parameter measurement circuitry 302 to have an impedance with both a resistive and a reactive part, and which appears to the defibrillation shock and measurement circuitry 304 to have a primarily resistive impedance.

Shown in FIG. 3A is that defibrillation unit 300 is used to gather empirical data by engaging in multiple trials pairing a measured patient parameter against a measured defibrillation impedance. In one implementation, energizing and measurement circuitry energizes electrodes 102 and 104 with a 62.5 kilohertz time-varying voltage signal, and thereafter measures the impedance of the human body generated in response to the 62.5 kilohertz time-varying voltage signal. Subsequent to such measurement, defibrillation shock and measurement circuitry 304 discharges a defibrillation pulse into the human body and utilizes well-known techniques drawn on the defibrillation energy discharged into the human body in order to determine a defibrillation impedance (e.g., see U.S. Pat. No. 5,999,852, "Defibrillation Method and Apparatus" incorporated herein by reference, and refer to the description of patient TTI (transthoracic impedance) measured during delivery of a defibrillation pulse).

As shown in FIG. 3A, subsequent to the gathering of such empirical data, the impedance "seen" by energizing and patient parameter measurement circuitry 302, depicted in graph 306 as "carrier frequency impedance" (CFI) along the vertical axis, can be graphed against the defibrillation "seen" by defibrillation shock and measurement circuitry 304, depicted in graph 306 as "defibrillation impedance" on the horizontal axis.

Figure 3B:
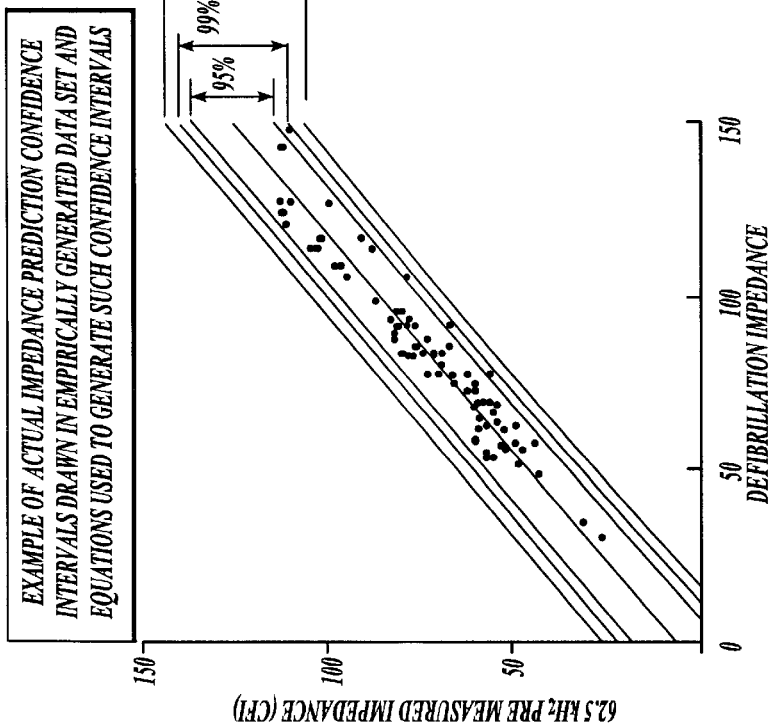
FIG. 3B shows an empirically generated data set and one implementation of equations utilized to derive impedance prediction confidence intervals shown therein.

Subsequent to graphing the empirically generated data which correlates the measured carrier frequency impedance against the measured defibrillation impedance, a best fit curve fitting algorithm (e.g., a least mean squares curve fitting algorithm) may be employed to draw a "best fit" curve through the data (e.g., line 312 of FIG. 3A). Thereafter, as shown in FIG. 3A, pairs of curves (e.g., curves 308 and 310) may be drawn about the best fit curve (illustrated as curve 312). In one embodiment, statistical techniques (e.g., statistical inference) are used which essentially ensure that the statistical distribution of impedance along lines drawn perpendicular to the carrier frequency impedance axis fall within the pairs of curves (this maneuver is illustrated graphically and mathematically in FIG. 3B). Notice that this maneuver is counter-intuitive in that while ultimately it will be the defibrillation impedance axis which is utilized to construct confidence interval curves, it is against the carrier frequency impedance axis that the statistical inference distribution is baselined, which is somewhat surprising in that it essentially reverses the ordinary line of thought typically utilized by those having ordinary skill in the art.

Referring to graph 306, measurement of the inaccuracy or variance is shown by the various paired curves about the best fit curve (e.g., curves 308, 310 about best-fit curve 312 can be used to designate an impedance prediction confidence interval.) Once such paired curves have been used to define impedance prediction confidence intervals, the various defibrillation current curves of graph 202 can be associated with prediction confidence levels. For example, the 95% impedance prediction confidence level defined by curve 308 of FIG. 3A is associated with curve 210 of FIG. 2. So long as the absolute maximum rating of at least one component of defibrillation unit 200 is above the upper (e.g., curve 210) 95% defibrillation prediction confidence level curve of the family of curves drawn on graph 202 of FIG. 2, the designer can be 95% certain that the circuitry of defibrillation unit 200 will be able to deliver the defibrillation pulse. Similarly, the 95% impedance prediction confidence level defined by curve 310 of FIG. 3A is associated with curve 208 of FIG. 2. So long as the lower (e.g., curve 208) 95% defibrillation prediction confidence level is above the defibrillation threshold, the designer can be greater than 95% certain that a patient at the specified defibrillation impedance will be defibrillated.

FIG. 3B shows an empirically generated data set and one implementation of equations utilized to derive impedance prediction confidence intervals shown therein. As noted, one aspect of the generation of impedance prediction confidence intervals is that the way in which they are generated and/or used herein goes "against the grain" of the way in which those skilled in the art are typically taught to generate and use such intervals. Accordingly, FIG. 3B shows an actual empirical data set along with actual mathematical equations utilized to generate the impedance prediction confidence intervals shown thereon. While the explanation of FIG. 3A is sufficient to teach how to generate the confidence intervals without undue experimentation, the inventors have chosen to include FIG. 3B as a specific example of the more general case described in relation to FIG. 3A so that those skilled in the art will be able to generate and use the impedance prediction confidence intervals shown and described herein with much less experimentation than ordinarily is required in the art.

As illustrated above, the inventors' scheme described herein allows design of defibrillation unit 200 with much lower current components than those necessary in the related art. In order to utilize a defibrillation unit so designed, a designer would preferably set the defibrillation energy source (e.g., a capacitor, bank of capacitors or other DC source) of defibrillation unit 200 to a voltage level such that defibrillation current discharged into a patient tracks the defined defibrillation prediction confidence a predicted-level curve family of graph 202 in a fashion such as will now be described. However, although the following processes and devices will be described in the context of defibrillation units designed in accord with the iterative design technique described above, it is to be understood that the processes and devices need not be utilized with a defibrillation unit so designed, and can instead be adapted to virtually any defibrillation unit whose electrical characteristics have been defined.

Figure 4A:
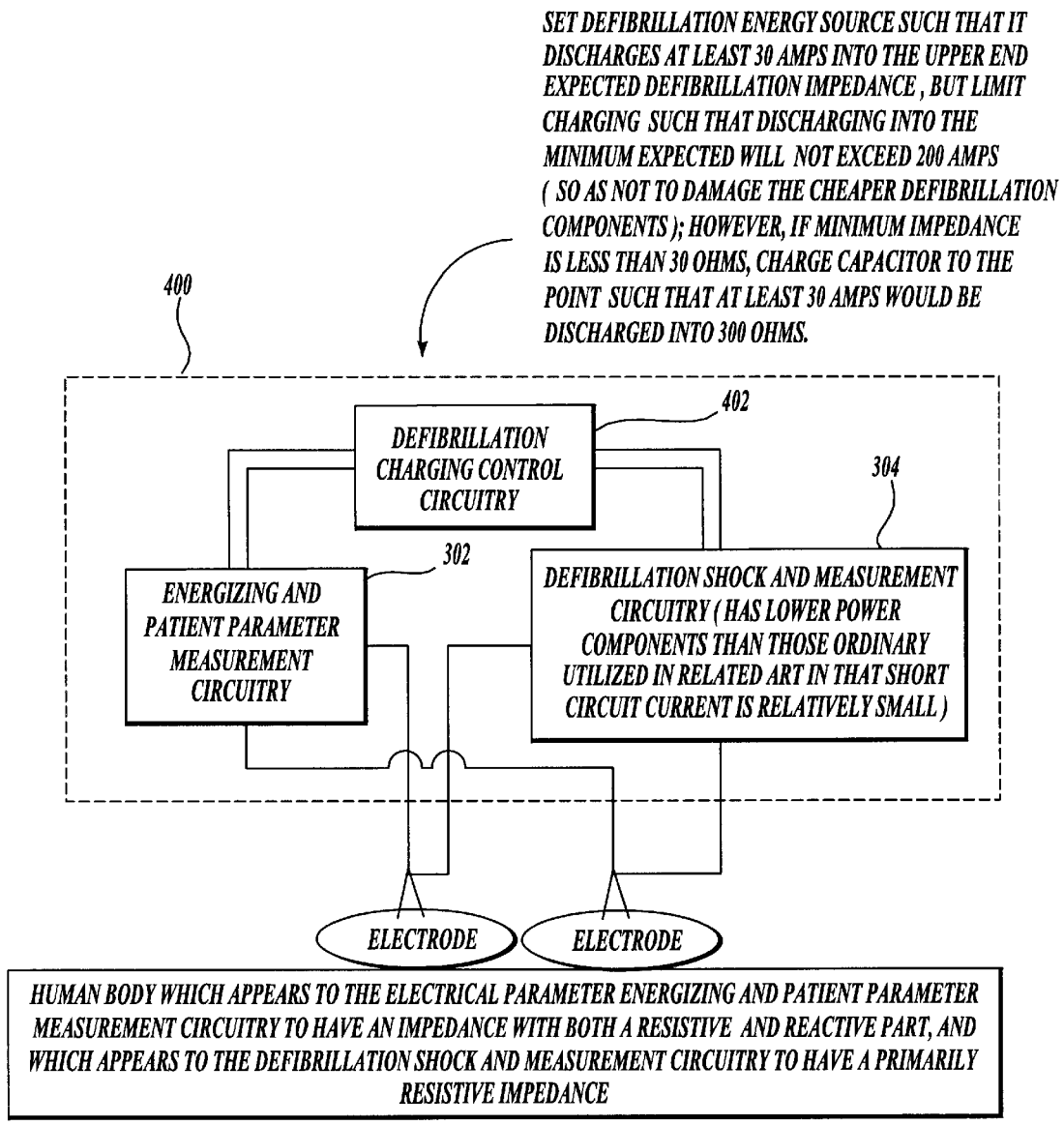
FIG. 4A shows a defibrillation unit 400 which has components functionally analogous to those shown in defibrillation unit 300, plus the addition of defibrillation charging control circuitry 402.

Referring now to FIG. 4A, shown is defibrillation unit 400 which has components functionally analogous to those shown in defibrillation unit 300, plus the addition of defibrillation charging control circuitry 402. As shown, in operation, defibrillation charging control circuitry 402 obtains the carrier frequency impedance measured by energizing and patient parameter measurement circuitry 302 and in response to such obtained carrier frequency impedance directs that defibrillation shock and measurement circuitry 304 set its defibrillation energy source such that a defined level of defibrillation energy will be discharged sufficient to meet whatever defibrillation prediction confidence level the system designer has defined. In one implementation, an attempt is made to deliver sufficient energy such that the defibrillation threshold of graph 202 is exceed and the value of the electrical parameter of interest (e.g., current) is not exceeded, so as to prevent damage at least to a specified prediction confidence level, while at the same time meeting the industry standard levels of defibrillation energy.

As has been described and which will be described in more detail below (e.g., FIGS. 5–12), devices and/or processes can be utilized with defibrillation units in order to allow such defibrillation units to provide acceptable levels of defibrillation and pass required short-circuit testing. For example, in one embodiment an amount of stored energy in defibrillation unit 400 is adjusted in response to a measured carrier frequency impedance such that current delivered will fall within the bounds of a defined family of curves such as curves 208, 210 shown in graph 202. FIG. 4B shows an example of one energy adjustment curve based on the foregoing described scheme, where the curve shown in FIG. 4B is based upon the empirically derived data set and family of curves shown and described in relation to FIG. 3B.

Those having ordinary skill in the art will recognize that it is known within the art that defibrillation units often store energy in capacitive structures, and thereafter discharge the energy stored in such capacitive structures into the patient. Those skilled in the art will also recognize that the energy stored in such capacitive structures as well as the maximum defibrillation current can be determined from said voltage and the patient's defibrillation impedance. Accordingly, if the voltage adjustment curve of FIG. 4B is implemented by defibrillation charging control circuitry 402, then the family of curves in graph 202 can be determined.

One implementation whereby voltage can be adjusted in response to a measured carrier frequency impedance is shown in FIG. 4B. Segment 450 has a constant charging voltage since in this region the associated 95% confidence prediction level of defibrillation impedance is less than zero. Since the defibrillation impedance physically cannot be less than zero, the worse case defibrillation impedance can be assumed to be zero. In this implementation, zero defibrillation impedance will result in 200 amps (the maximum the electrical components of this implementation can accommodate) if the charging voltage is set to that indicated in segment 450. (This is due to an assumed 5 ohms internal impedance.) FIG. Segment 452 shows a voltage compensation region in response to measured carrier frequency impedance. Segment 454 shows no voltage compensation such as has been described herein since segment 454 is above defibrillation energy baseline impedance 456 and hence is not the subject of the discussion herein. That is, the resulting current is substantially guaranteed to be below a defined maximum current as indicated by graph 202.

Figure 4C:
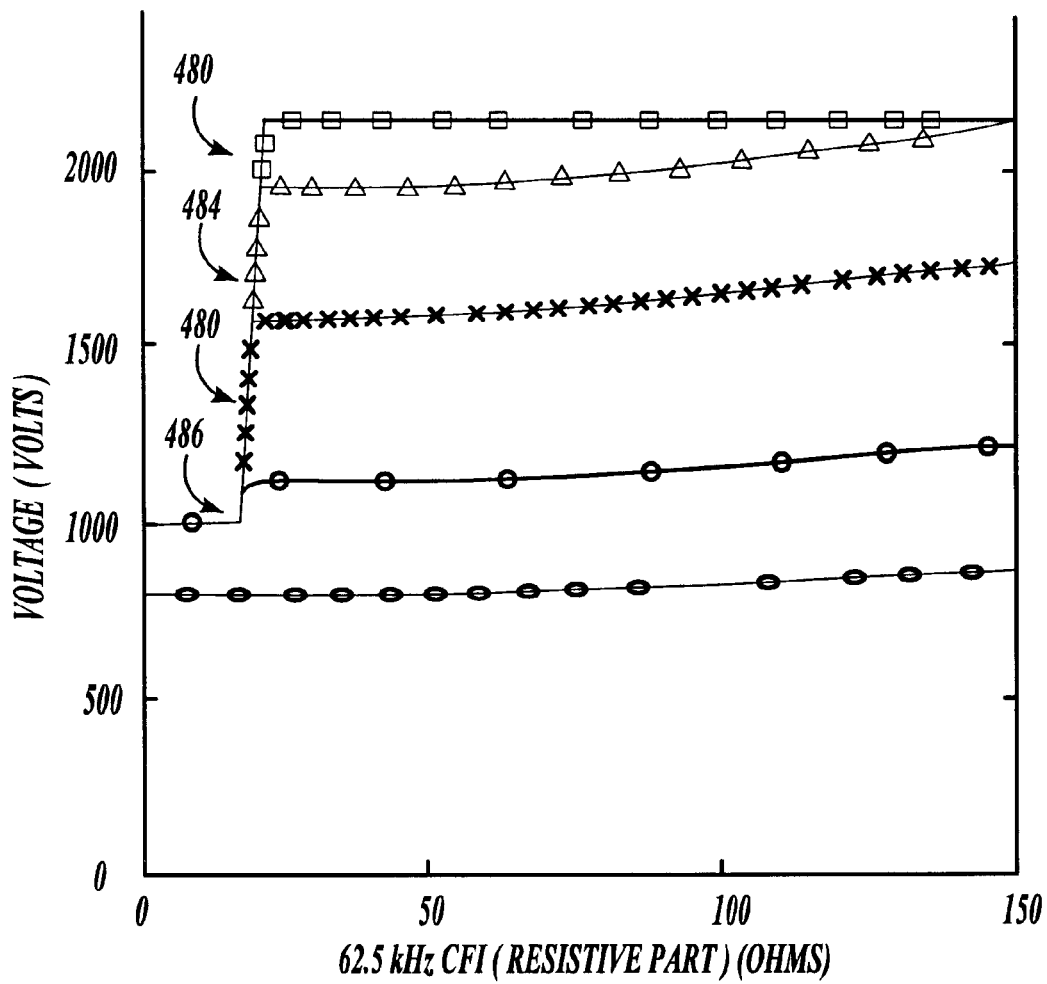
FIG. 4C shows a scaled version of the FIG. 4B, showing the designed energy storage capacitor voltage for various energies in the 0 to 150 ohm patient-impedance range.

Referring now to FIG. 4C, shown is a scaled version of the energy adjustment curve of FIG. 4B, showing energy storage capacitor voltage for various energies in the 0 to 150 ohm patient-impedance range. In FIG. 4C the voltage compensation region below 21.5 ohms is designed from a linear approximation to the lower 99.9% prediction interval curve of FIG. 3B, a simplification which has a maximum of 1 volt error.

Figure 5:
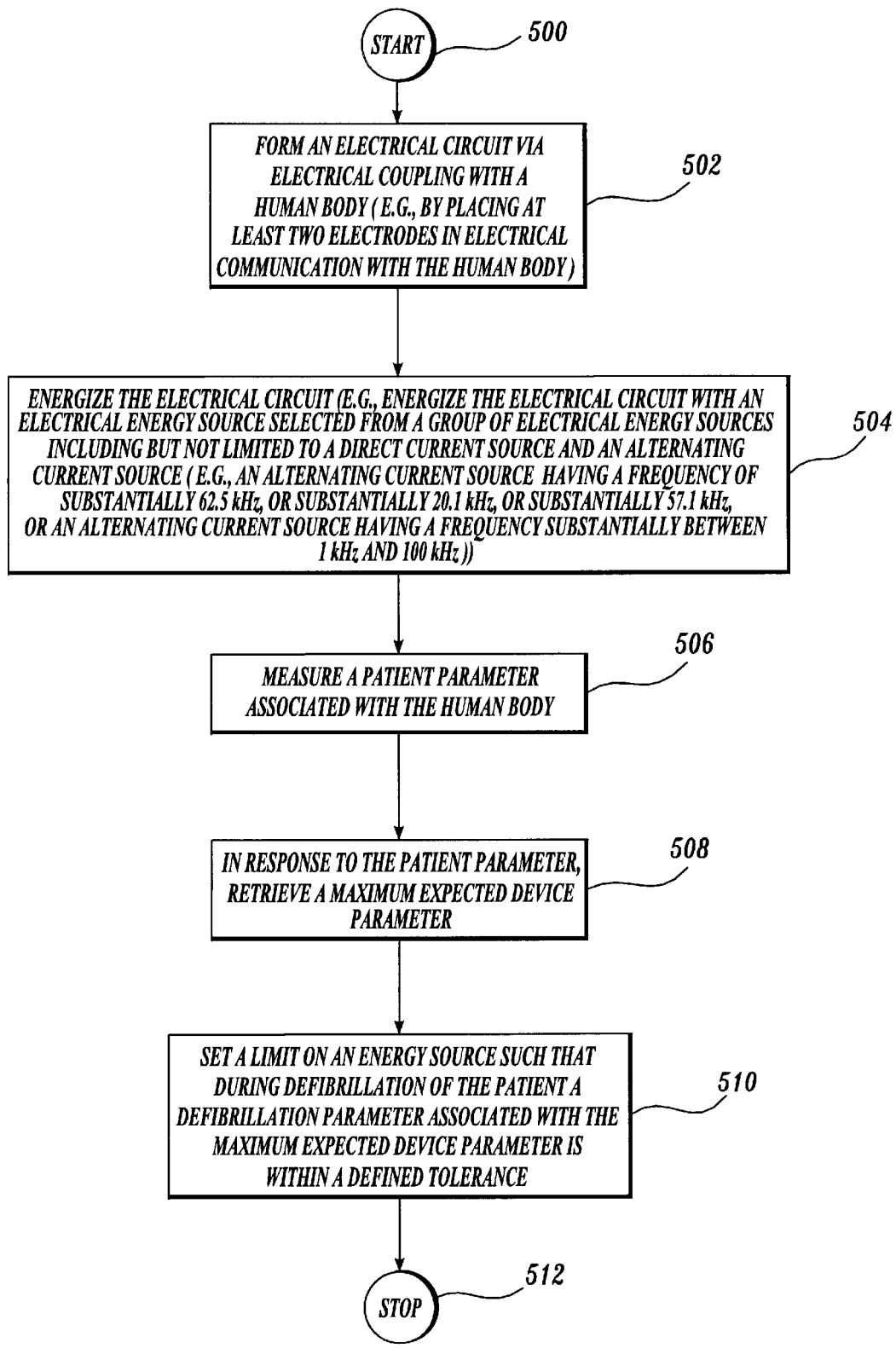
FIG. 5 shows a high-level logic flowchart illustrating a process which utilizes one or more of the herein described ideas and concepts.

Referring now to FIG. 5 shown is a high-level logic flowchart illustrating a process which utilizes one or more of the herein described ideas and concepts. Block 500 shows the start of the process. Block 502 shows forming an electrical circuit via coupling with a human body (e.g., placing external defibrillation electrodes 100, 102 of defibrillation unit 200 onto a human body such as shown and described in relation to FIG. 4A). It should be noted that the use of external electrodes is merely exemplary and that the methods and systems described herein can be adapted for use with implantable internal defibrillators via the use of reasonable experimentation well within the ambit of those having ordinary skill in the art. Block 504 depicts energizing the electrical circuit formed with the human body via an energy source selected from a group including, but not limited to, a direct current source and an alternating current source. (In one implementation, the alternating current source has a frequency of 62.5 kilohertz such as was shown and described in relation to the energizing and patient parameter measurement circuitry 302 of FIG. 4A; however, in other implementations, the alternating current source has frequency of substantially 62.5 kHz, or substantially 20.1 kHz, or substantially 57.1 kHz, and in yet other implementations the alternating current source has a frequency substantially between 1 kHz and 100 kHz.) Block 506 depicts measuring a patient parameter associated with the human body (e.g., such as energizing and patient parameter measurement circuitry 302 measuring the carrier frequency impedance such as was shown and described in relation to FIGS. 3 and 4).

Block 508 depicts that in response to the measured patient parameter, a maximum expected device parameter is retrieved (e.g., such as was described in relation to defibrillation charging control circuitry 402 of FIG. 4A).

Block 510 shows setting a limit on an energy source (e.g., a defibrillation energy source) such that during defibrillation of the patient a defibrillation parameter associated with the maximum expected device parameter is within a defined tolerance (e.g., attempting to set the energy source such that it will deliver an industry-required amount of defibrillation energy into the highest defibrillation impedance likely to be encountered, but limiting the charging such that at the minimum impedance likely to be encountered at the defined confidence level, a defined circuit parameter of interest is not likely to be exceeded, such as was shown and described in relation to FIGS. 4A, 4B and 4C). Block 512 shows the end of the process.

Figure 6:
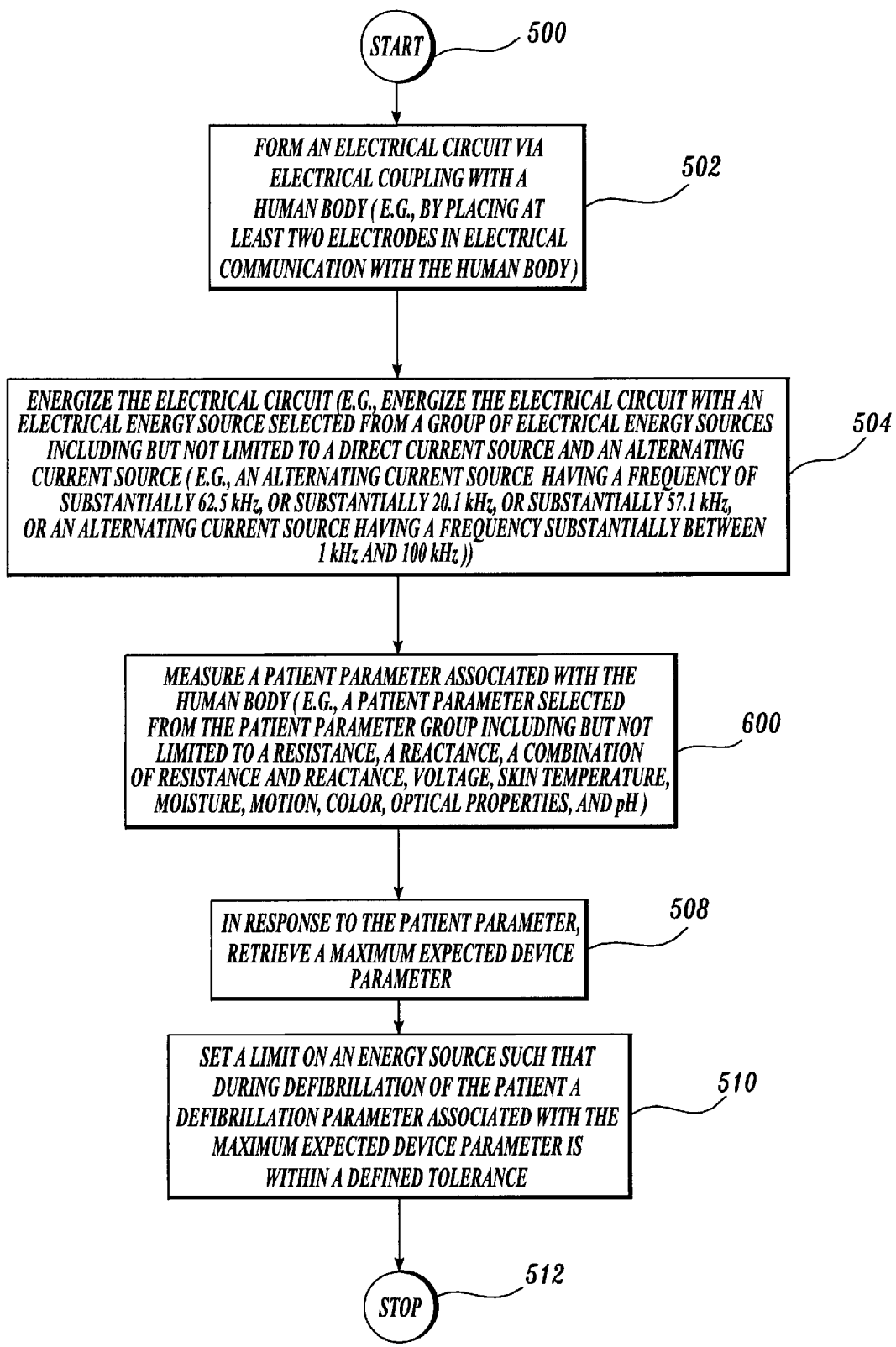
FIG. 6 shows an implementation of the high-level logic flowchart of FIG. 5, wherein it is shown that in one embodiment of method 506 the measured patient parameter is selected from the group including, but not limited to, a resistance, a reactance, a combination of resistance and reactance, voltage, skin temperature, moisture, motion, color, optical properties, and pH; that is, the implementation of FIG. 6 shows that the carrier frequency impedance measured can include both reactive and resistive parts either taken alone or in combination.

Referring now to FIG. 6 shown is an implementation of the high-level logic flowchart of FIG. 5, wherein it is shown that in one embodiment of method 506 the measured patient parameter is selected from the patient-parameter group including, but not limited to, a resistance, a reactance, a combination of resistance and reactance, voltage, skin temperature, moisture, motion, and optical properties, and pH; that is, the implementation of FIG. 6 shows that the carrier frequency impedance measured can include both reactive and resistive parts of the carrier frequency impedance either taken alone or in combination, and that other manners of measuring patient parameters are also contemplated. The remaining blocks of FIG. 6 function substantially as described elsewhere above.

Figure 7:
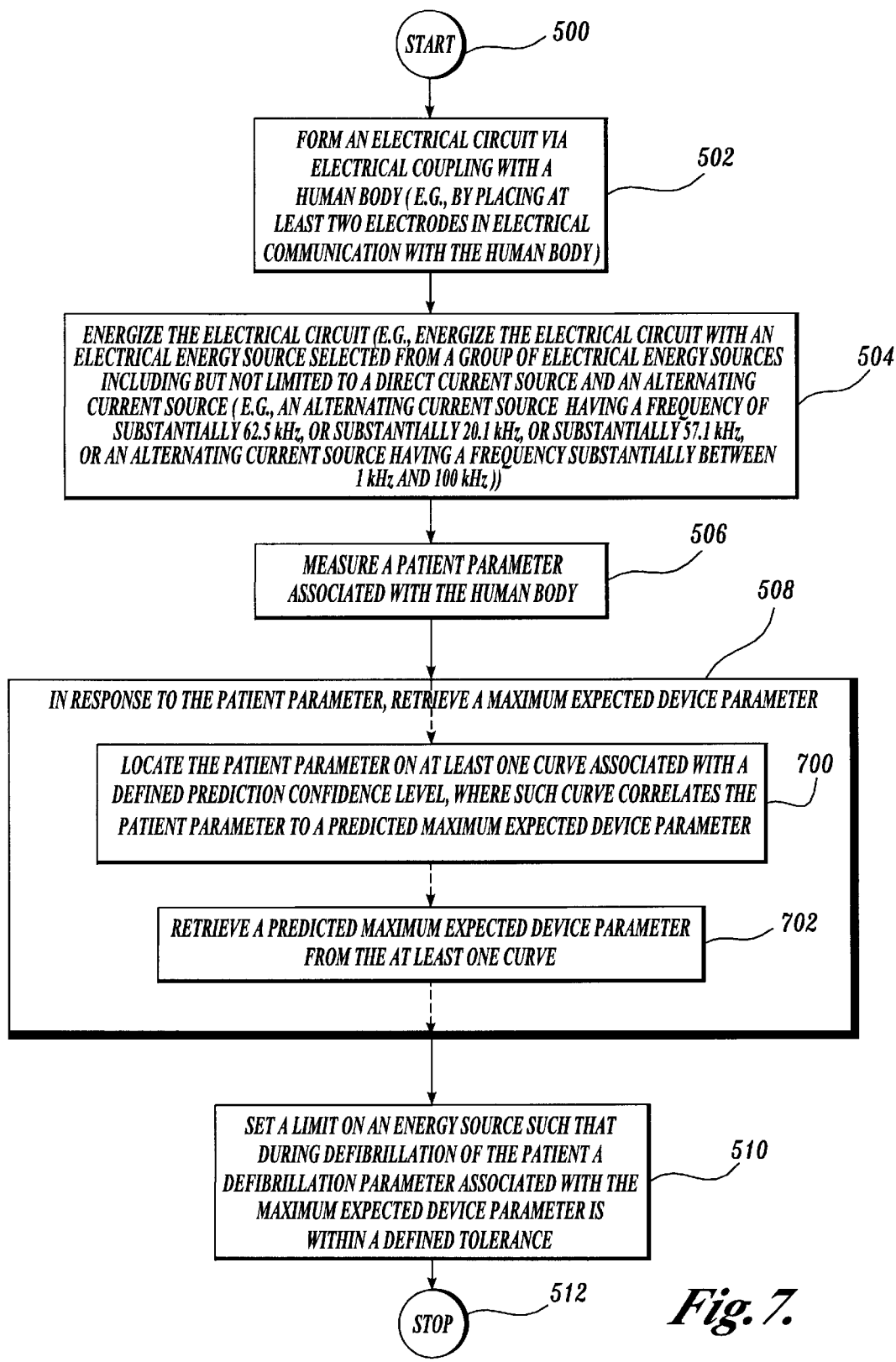
FIG. 7 shows an implementation of the high-level logic flowchart shown in FIG. 5.

Referring now to FIG. 7 shown is an implementation of the high-level logic flowchart shown in FIG. 5. Depicted in FIG. 7 is one implementation block 508 that includes the substeps of blocks 700 and 702. Block 700 shows that in one implementation retrieving a maximum expected device parameter can include, but is not limited to, locating the patient parameter on at least one curve associated with a defined prediction confidence level, where such curve correlates the patient parameter to a predicted maximum expected device parameter (e.g., locating a patient parameter on the graph of FIG. 2). Block 702 shows retrieving a predicted maximum expected device parameter from the at least one curve (e.g., locating at least one value on curve 210 of FIG. 2). The remaining blocks of FIG. 7 function substantially as described elsewhere herein.

Figure 8:
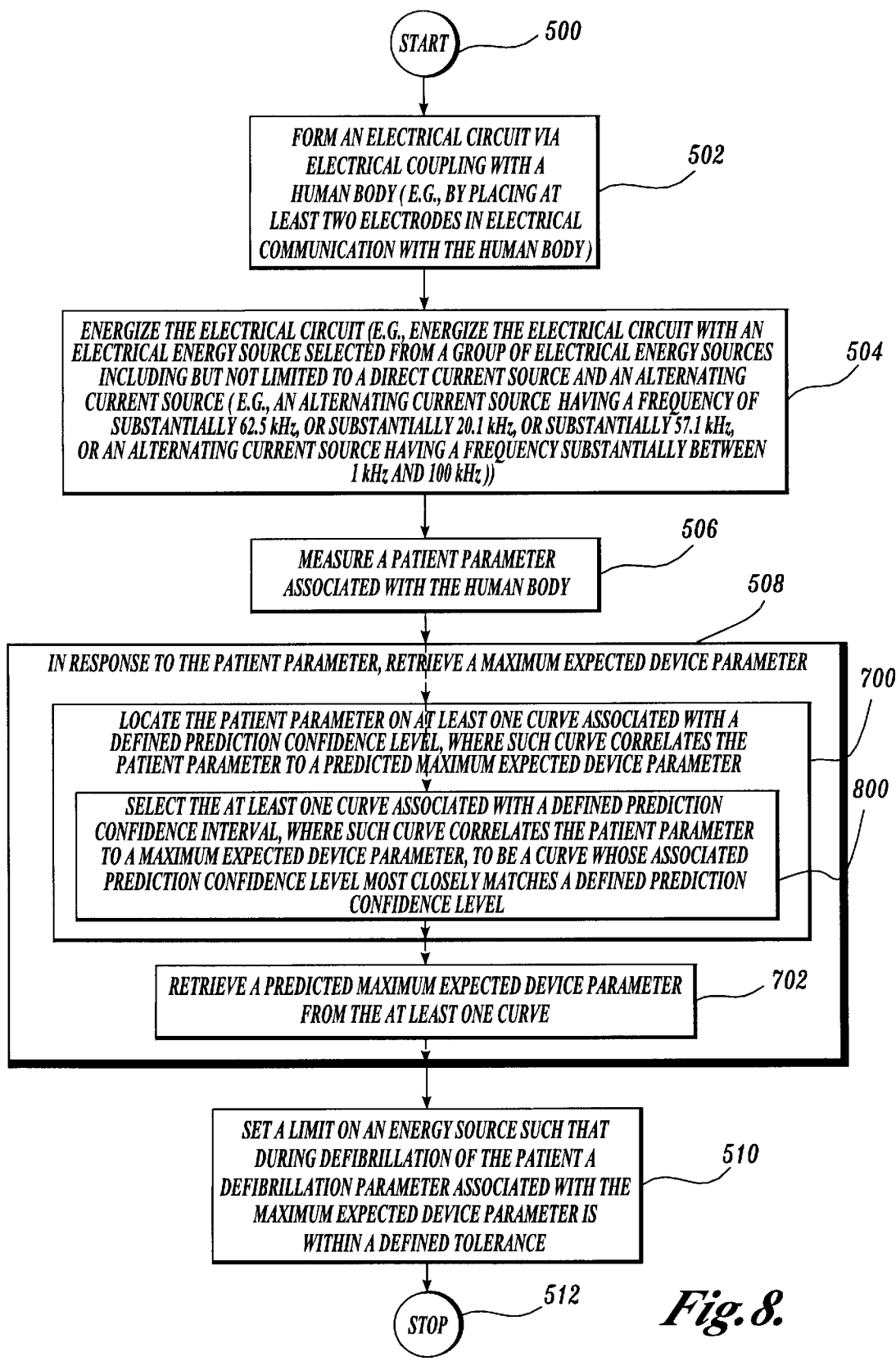
FIG. 8 shows an implementation of the high-level logic flowchart shown in FIG. 7.

With reference now to FIG. 8, shown is an implementation of the high-level logic flowchart shown in FIG. 7. Depicted is an implementation wherein block 700 is shown to include sub-block 800 of selecting the at least one curve associated with a defined prediction confidence interval, where such curve correlates the patient parameter to a maximum expected device parameter, to be a curve whose associated prediction confidence level most closely matches a defined prediction confidence level—in one implementation, this is achieved by accessing one of a family of curves analogous to those shown and described in relation to graph 202. The remaining blocks of FIG. 8 function substantially as described elsewhere herein.

Figure 9:
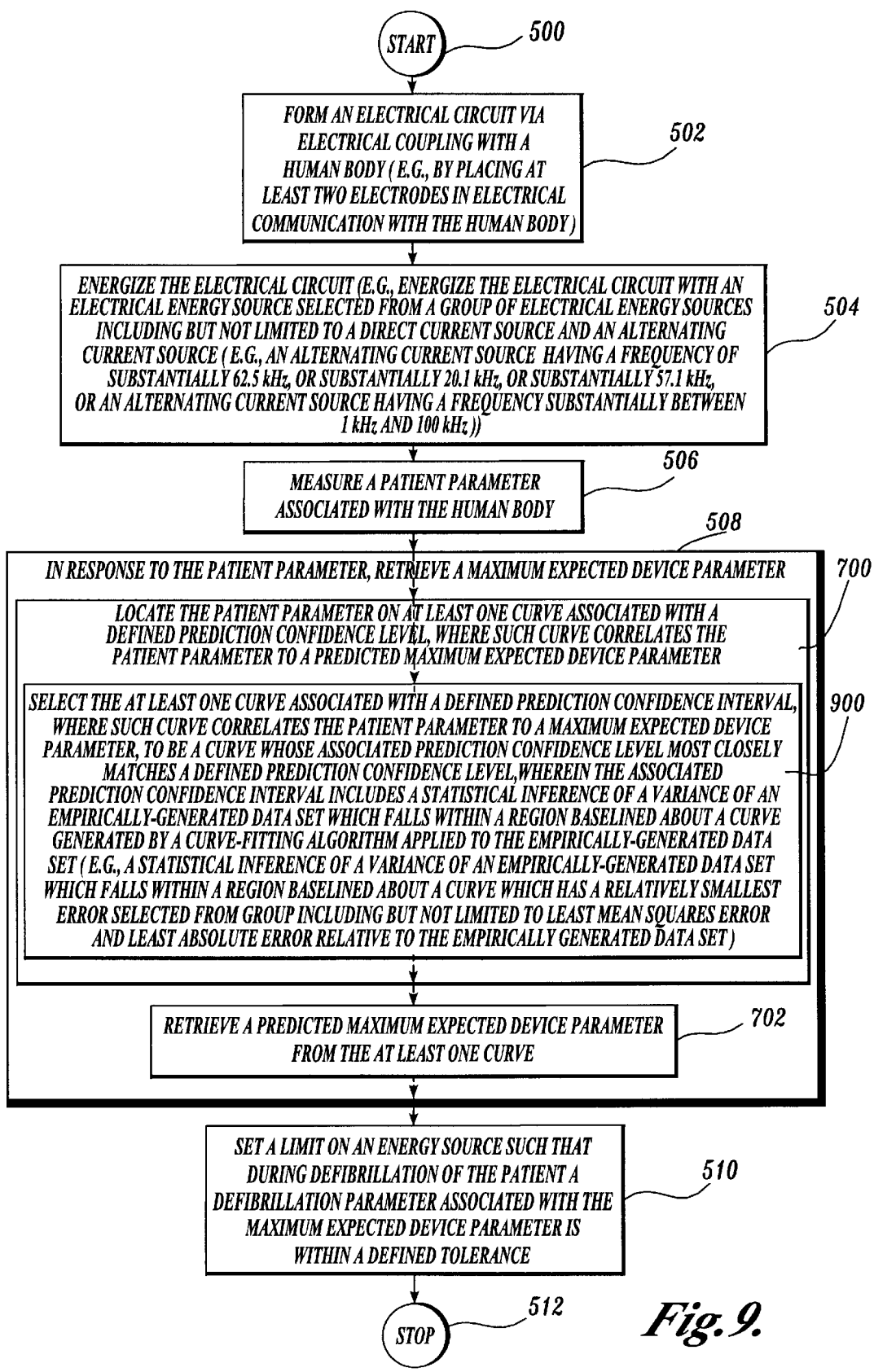
FIG. 9 depicts an implementation of the high-level logic flowchart shown in FIG. 8.

With reference now to FIG. 9, depicted is an implementation of the high-level logic flowchart shown in FIG. 8. Illustrated is that in one embodiment the associated prediction confidence level of block 900 includes a statistical inference of a variance of an empirically-generated data set which falls within a region baselined about a curve generated by a curve-fitting algorithm applied to the empirically generated data set (e.g., such as was shown and described in relation to FIGS. 3A and 3B, above). As shown and described in relation to FIGS. 3A and 3B, in one implementation this is achieved via a statistical inference of an empirically-generated data set which falls within a region baselined about a curve which has a relatively smallest least mean squares error, or least absolute error, relative to the empirically generated data set. The remaining blocks of FIG. 9 function substantially in as described elsewhere herein.

Figure 10:
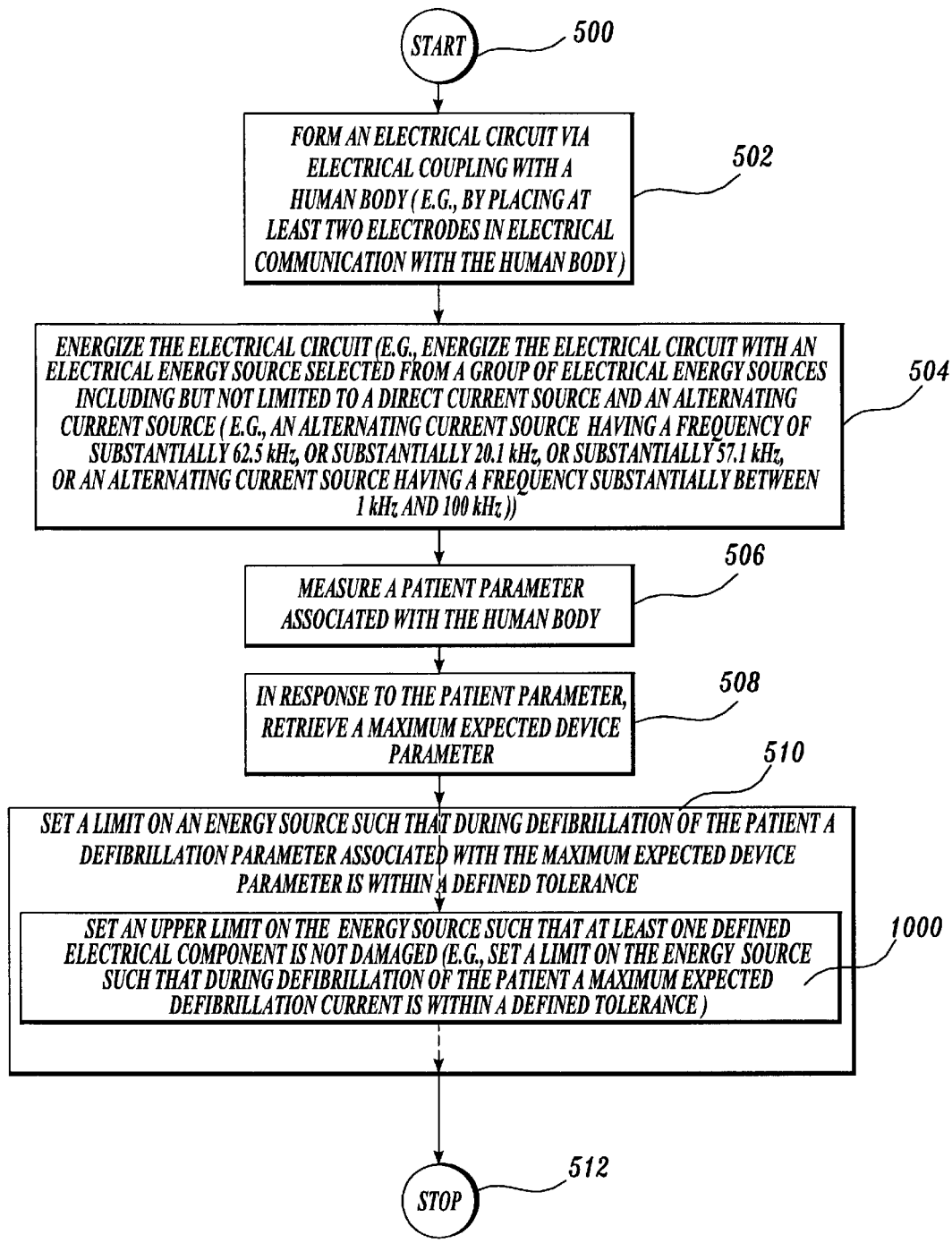
FIG. 10 shows an implementation of the high-level logic flowchart of FIG. 5.

Referring now to FIG. 10, shown is an implementation of the high-level logic flowchart of FIG. 5. Depicted is that in one implementation block 510 can include setting an upper limit on the energy source such that at least one defined electrical component is not damaged (e.g., setting a limit on the energy source such that during defibrillation of the patient a maximum expected defibrillation current is within a defined tolerance), such as was discussed in relation to FIGS. 4A, 4B and 4C above, where an attempt is made to set the source such that the person with the highest likely impedance to be encountered will still receive sufficient current to defibrillate while also at the lowest likely impedance to be encountered, a defined absolute maximum of an electrical component of a defibrillation unit (e.g., current of defibrillation unit 200) is not exceeded, all while maintaining the industry standard level of defibrillation energy. The remaining blocks of FIG. 10 function substantially as described elsewhere herein.

Figure 11:
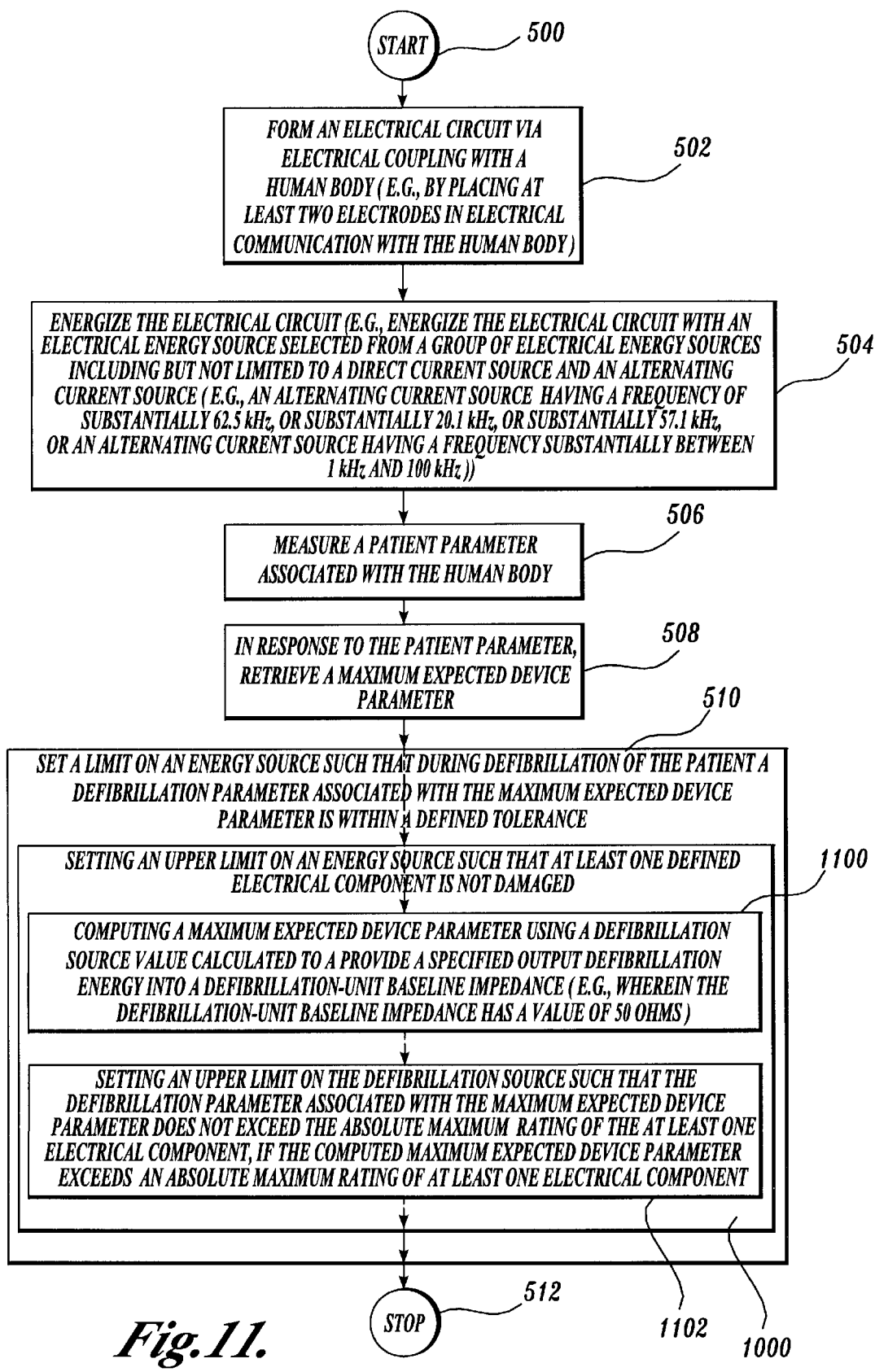
FIG. 11 shows that in one implementation, block 1000 of FIG. 10 can include block 1100 and block 1102.

Referring now to FIG. 11 shown is that in one implementation, block 1000 of FIG. 10 can include block 1100 and block 1102. Block 1100 shows computing a maximum expected device parameter using a defibrillation source value calculated to provide a specified output defibrillation energy into a defibrillation-unit baseline impedance (e.g., wherein the defibrillation-unit baseline impedance has a value of 50 ohms). Block 1102 shows setting an upper limit on the defibrillation source such that the defibrillation parameter associated with the maximum expected device parameter does not exceed the absolute maximum rating of the at least one electrical component, if the computed maximum expected device parameter exceeds an absolute maximum rating of at least one electrical component. The remaining blocks of FIG. 11 function substantially as described elsewhere herein.

Figure 12:
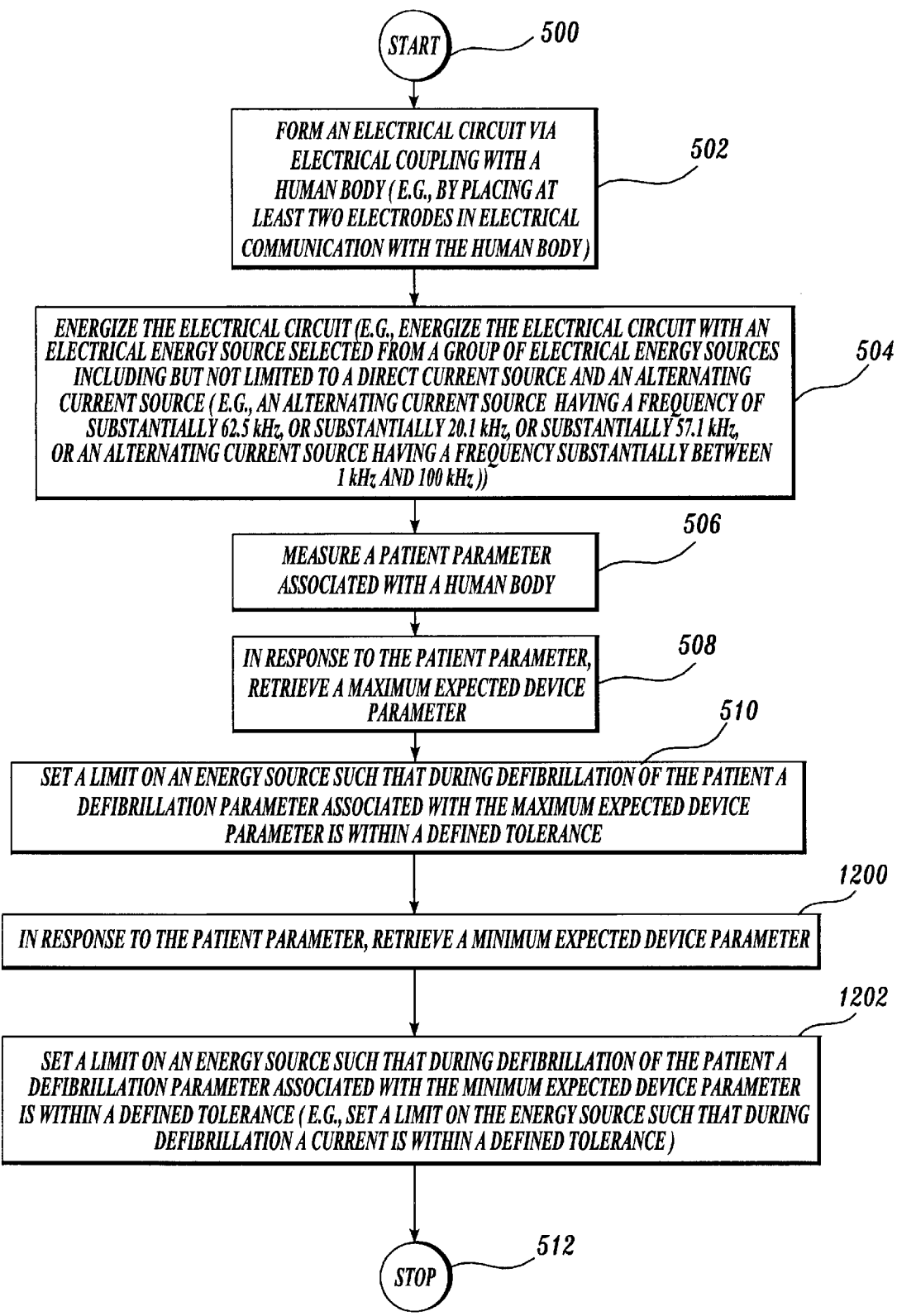
FIG. 12 shows an alternate implementation of the high-level logic flowchart of FIG. 5.

With reference now to FIG. 12, shown is an alternate implementation of the high-level logic flowchart of FIG. 5. Depicted is that in one implementation the high level logic flowchart further includes blocks 1200 and 1202. Block 1200 depicts that, in response to the measured patient parameter, a minimum expected device parameter is retrieved. Block 1202 illustrates setting a limit on an energy source such that during defibrillation of the patient a defibrillation parameter associated with the minimum expected device parameter is within a defined tolerance (e.g., set a limit on the energy source such that during defibrillation a current is within a defined tolerance). The remaining blocks of FIG. 12 function substantially as described elsewhere herein.

Figure 13:
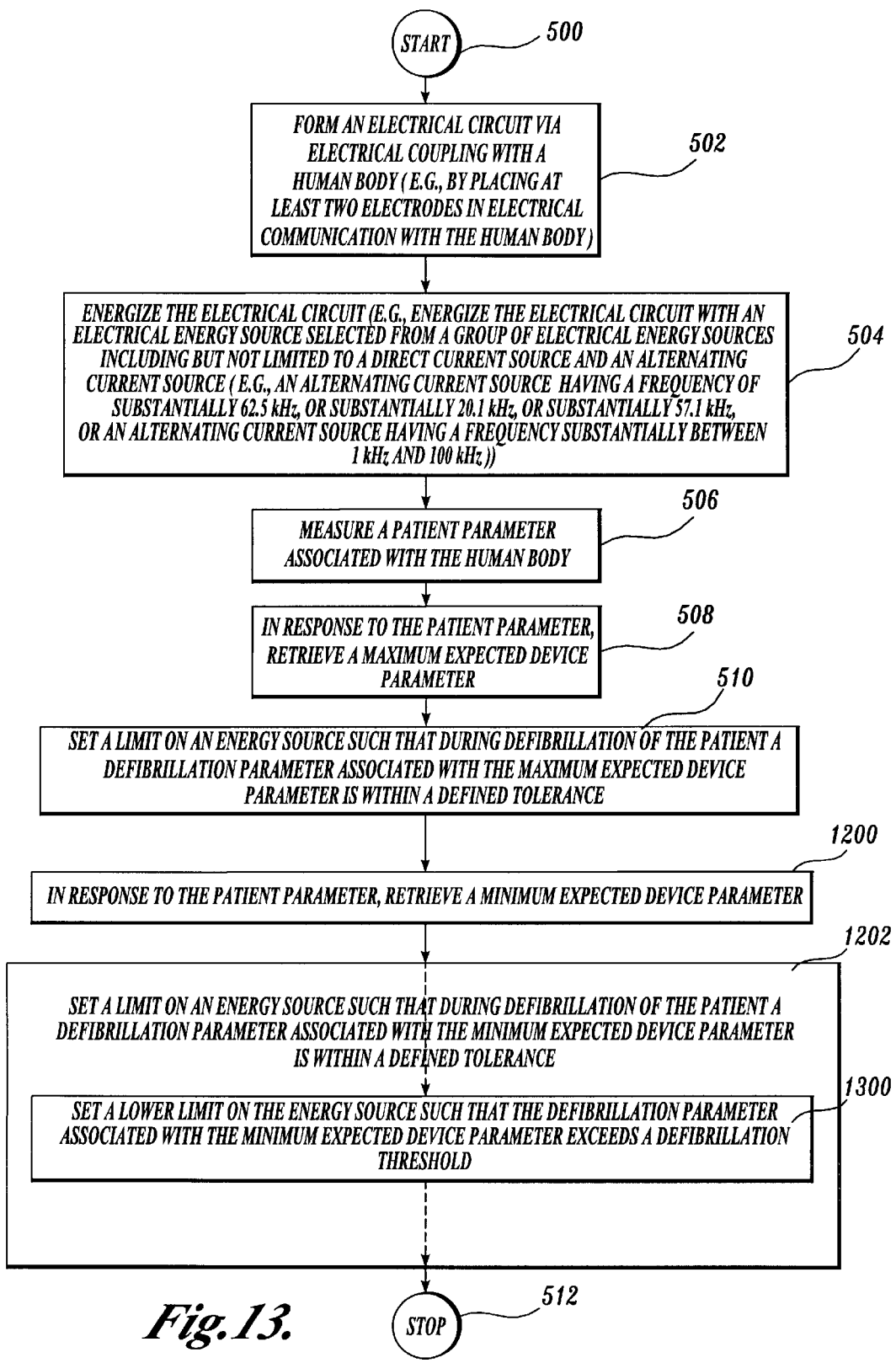
FIG. 13 shows an implementation of the high-level logic flowchart of FIG. 12.

Referring now to FIG. 13 shown is an implementation of the high-level logic flowchart of FIG. 12. Depicted is that in one implementation block 1202 can include setting a lower limit on the energy source such that the defibrillation parameter associated with the minimum expected device parameter exceeds a defibrillation threshold (e.g., such as was discussed in relation to FIGS. 4A, 4B and 4C above, where an attempt is made to set the source such that the person with the highest likely impedance to be encountered will still receive sufficient current to defibrillate while also at the lowest likely impedance to be encountered a defined absolute maximum of an electrical component of a defibrillation unit (e.g., current of defibrillation unit 200) is not exceeded, all while maintaining the industry standard level of defibrillation energy). The remaining blocks of FIG. 13 function substantially as described elsewhere herein.

Figure 14:
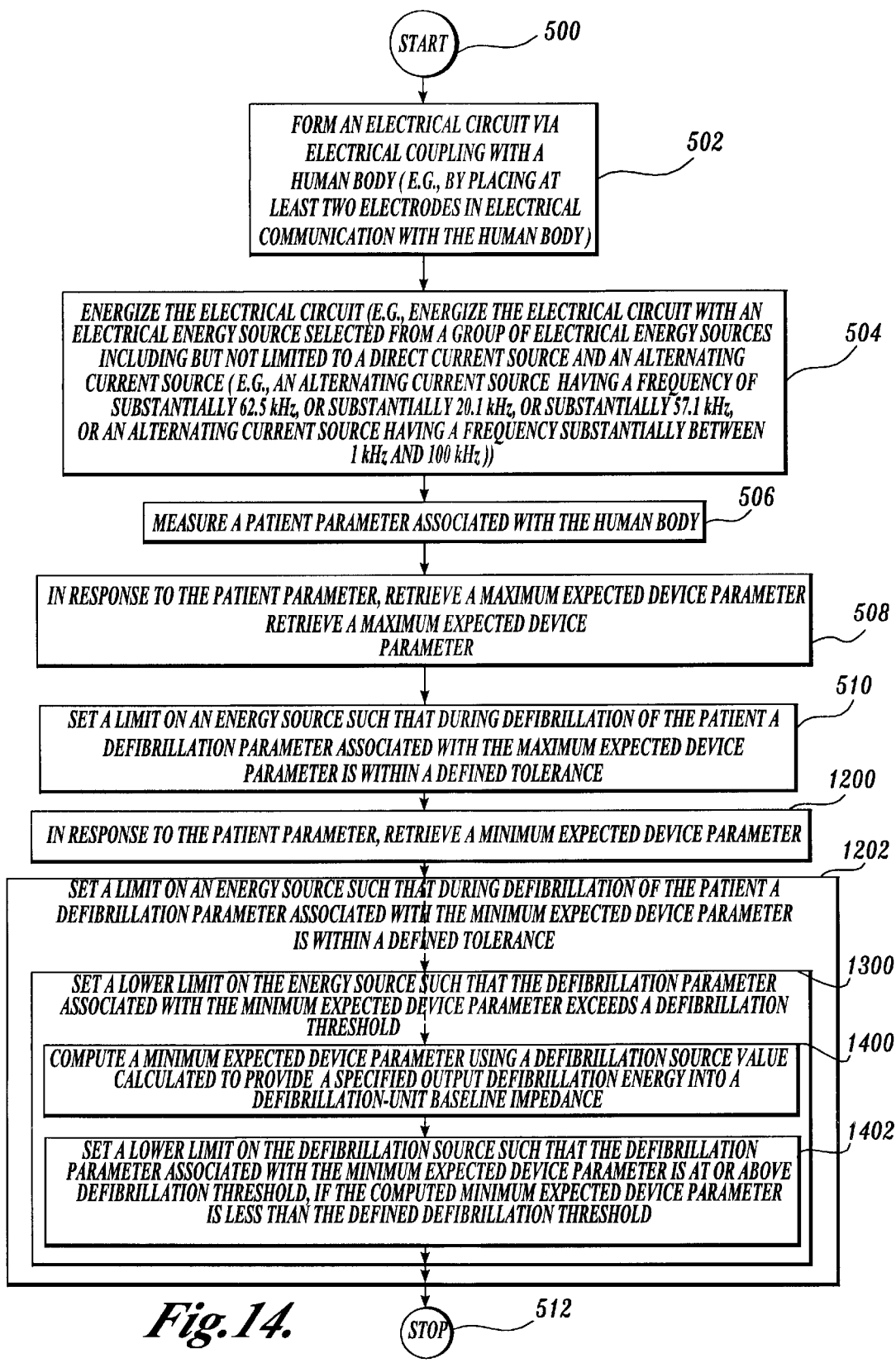
FIG. 14 shows that in one implementation, block 1300 of FIG. 13 can include block 1400 and block 1402.

Referring now to FIG. 14, shown is that in one implementation, block 1300 of FIG. 13 can include block 1400 and block 1402. Block 1400 shows computing a minimum expected device parameter using a defibrillation source value calculated to provide a specified output defibrillation energy into a defibrillation-unit baseline impedance (e.g., wherein the defibrillation-unit baseline impedance has a value of 50 ohms). Block 1402 shows setting a lower limit on the defibrillation source such that the defibrillation parameter associated with the minimum expected device parameter is at or above the defibrillation threshold, if the computed minimum expected device parameter is less than the defined defibrillation threshold. The remaining blocks of FIG. 14 function substantially as described elsewhere herein.

Those skilled in the art will recognize that the state of the art has progressed to the point where there is little distinction left between hardware and software implementations of certain aspects of systems; the use of hardware or software is generally (but not always, in that in certain contexts the choice between hardware and software can become significant) a design choice representing cost vs. efficiency tradeoffs. The foregoing detailed description has set forth various embodiments of the devices and/or processes via the use of block diagrams, flowcharts, and examples. Insofar as such block diagrams, flowcharts, and examples contain one or more functions and/or operations, it will be understood as known by those within the art that each function and/or operation within such block diagrams, flowcharts, or examples can be implemented, individually and/or collectively, by a wide range of hardware, software, firmware, or any combination thereof. In one embodiment, the present invention may be implemented via Application Specific Integrated Circuits (ASICs). However, those skilled in the art will recognize that the embodiments disclosed herein, in whole or in part, can be equivalently implemented in standard integrated circuits, as a computer program running on a computer, as a program running on a processor, as firmware, or as virtually any combination thereof and that designing the circuitry and/or writing the code for the software or firmware would be well within the skill of one of ordinary skill in the art in light of this disclosure. In addition, those skilled in the art will appreciate that the mechanisms of the present invention are capable of being distributed as a program product in a variety of forms, and that an illustrative embodiment of the present invention applies equally regardless of the particular type of signal bearing media used to actually carry out the distribution. Examples of a signal bearing media include but are not limited to the following: recordable type media such as Random Access Memory (RAM), flash memory, floppy disks, hard disk drives, CD ROMs, digital tape, and transmission type media such as digital and analogue communication links using TDM or IP based communication links (e.g., packet links).

In a general sense, those skilled in the art will recognize that the various embodiments described herein which can be implemented, individually and/or collectively, by a wide range of hardware, software, firmware, or any combination thereof can be viewed as being composed of various types of "electrical circuitry." Consequently, as used herein "electrical circuitry" includes but is not limited to electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially effects a process(es) describer herein, or a microprocessor configured by a computer program which at least partially effects a process(es) described herein), electrical circuitry forming a memory device (e.g., any and all forms of data processing memory), and electrical circuitry forming a communications device (e.g., a modem, communications switch, or optical-electrical equipment).

Figure 15:
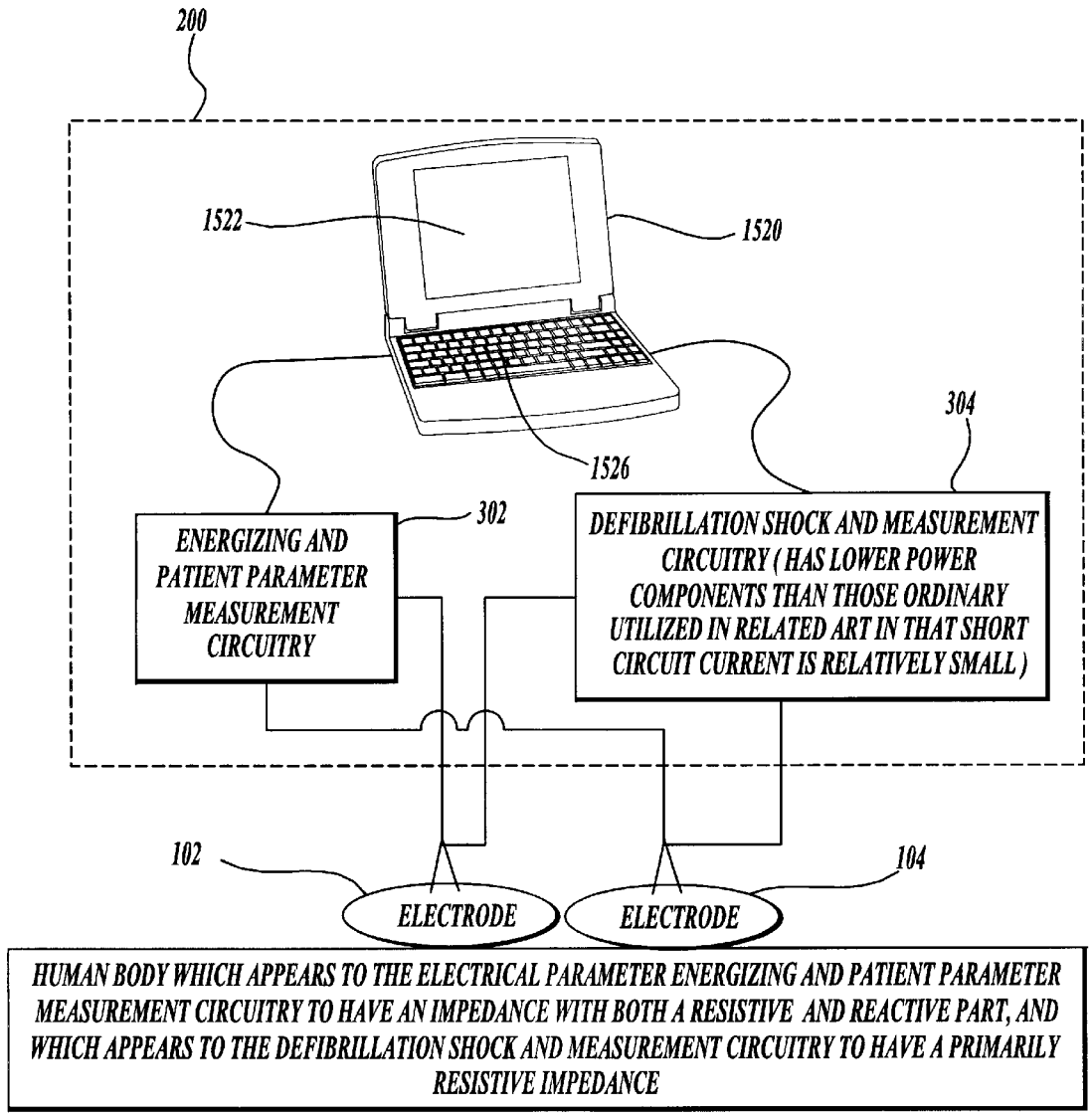
FIG. 15 depicts a pictorial representation of a processor-based system with which illustrative embodiments of the devices and/or processes described herein may be implemented via virtually any combination of software, hardware, and firmware with only minimal experimentation by those having ordinary skill in the art.

Those skilled in the art will recognize that it is common within the art to describe devices and/or processes in the fashion set forth herein, and thereafter use standard engineering practices to integrate such described devices and/or processes into defibrillation units. That is, the devices and/or processes described herein can be integrated into defibrillation units via a reasonable amount of experimentation well within the ambit of those having even a passing familiarity with the art. FIGS. 13, 14, and 15 show example representations of a processor-based defibrillation unit into which the described devices and/or processes may be integrated with a reasonable amount of experimentation. However, those skilled in the art will appreciate that implementations of devices and processes described herein are not limited to such implementations since, as has been explained above, the state of the art is now such that processes or devices can be implemented in virtually any combination of hardware, software, or firmware.

With reference now to FIG. 15, a pictorial representation of a processor-based system is depicted with which illustrative embodiments of the devices and/or processes described herein may be implemented via virtually any combination of software, hardware, and firmware with only minimal experimentation by those having ordinary skill in the art. It should be noted that a graphical user interface systems (e.g., Microsoft Windows 98 or Microsoft Windows NT operating systems) and methods can be utilized with the data processing system depicted in FIG. 15. Defibrillation unit 200 is depicted which includes data processing system 1520 (which is intended to be exemplary of virtually any processor based system). Data processing system 200 includes a system unit housing 1522, video display device 1524, keyboard 1526, a mouse (not shown), and a microphone (not shown). Data processing system 1520 is shown interfacing with and controlling energizing and parameter measurement circuitry 302 and defibrillation shock and measurement circuitry 304 in accordance with the teachings herein via techniques notorious within the art. Data processing system 1520 may be implemented utilizing any suitable computer such as a DELL® portable computer system, a product of Dell Computer Corporation, located in Round Rock, Tex.; Dell is a trademark of Dell Computer Corporation. Energizing and patient parameter measurement circuitry 302 and defibrillation shock and measurement circuitry 304 may be implemented utilizing circuitry produced by vendors well known to those having ordinary skill in the art such as Fairchild Semiconductor (e.g., their 74HC74, Dual D Flip Flop), Analog Devices (e.g., their AD8602DRM, Operational Amplifier), Vishay Dale Electronics (e.g., their Thick Film Surface Mount Resistor).

With reference now to FIG. 16, depicted is a pictorial representation of a processor-based system with which illustrative embodiments of the devices and/or processes described herein may be implemented via virtually any combination of software, hardware, and firmware with only minimal experimentation by those having ordinary skill in the art. The defibrillation unit 1610 includes impedance measuring circuit 1611, switch 1613, capacitor bank 1615, energy dump 1616, energy source 1617, defibrillator control circuit 1619, memory 1621, microprocessor 1623, energy selector 1625, and patient electrodes 1627a and 1627b.

The patient electrodes 1627a and 1627b may be hand-held electrode paddles or adhesive electrode pads placed on the skin of a patient. The patient's body or heart provides an electrical path between the electrodes. When using hand-held electrode paddles, the defibrillator or operating instructions preferably prompt the operator to hold and retain the paddles firmly on the patient's thorax throughout the impedance measurement and defibrillation procedure of the present invention.

The energy selector 1625 supplies energy setting information to the microprocessor 1623 and instructs the defibrillator regarding the defibrillation pulse energy to be delivered to a patient. While the energy selector 1625 can be in the form of a continuous dial, in a preferred embodiment the energy selector 1625 permits selection of an energy level from a set number of discrete energy levels, such as 100 joules, 200 joules, 300 joules, and 360 joules, for example. If desired, such as in the case of an automated external defibrillator with preprogrammed energy levels, the energy selector 25 could be eliminated, and replaced by pre-programmed levels.

The patient electrodes 1627a and 1627b are connected to the switch 1613 via conductors 1631a and 1631b. The switch 1613 couples the electrodes 1627a and 1627b to either the input of the impedance measuring circuit 1611 or to the output of the capacitor bank 1615, based on the state of a control signal received from the microprocessor 1623. The switch is of conventional design and may be formed of electrically-operated relays or solid state devices.

Those skilled in the art will appreciate that the hardware depicted in FIGS. 15, and 16 may vary for specific applications. For example, other peripheral devices such as optical disk media, audio adapters, video cameras such as those used in videoconferencing, or programmable devices, such as PAL or EPROM programming devices well-known in the art of computer hardware, and the like may be utilized in addition to or in place of the hardware already depicted.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that if a specific number of an introduced claim element is intended, such an intent will be explicitly recited in the claim, and in the absence of such recitation no such intent is present. For example, as an aid to understanding, the following appended claims may contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an;" the same holds true for the use of definite articles used to introduce claim elements. In addition, even if a specific number of an introduced claim element is explicitly recited, those skilled in the art will recognize that such recitation should typically be interpreted to mean at least the recited number (e.g., the bare recitation of "two elements," without other modifiers, typically means at least two elements, or two or more elements).

The embodiments of the invention in an exclusive property or privilege is claimed are defined as follows:

1. A method comprising:
    measuring a patient parameter associated with a human body;
    in response to the patient parameter, locating the patient parameter on at least one curve associated with a defined prediction confidence level, where such curve correlates the patient parameter with a predicted maximum expected device parameter;
    retrieving a predicted maximum expected device parameter from the at least one curve; and
    setting a limit on an energy source such that during defibrillation of the patient a defibrillation parameter associated with the maximum expected device parameter is within a defined tolerance.

2. The method of claim 1, further comprising:
    measuring a patient parameter associated with a human body by forming an electrical circuit with a human body via electrical coupling with a human body.

3. The method of claim 2, wherein said measuring a patient parameter associated with a human body by forming an electrical circuit with the human body via electrical coupling with a human body comprises:
    energizing an electrical circuit with a human body via an energy source selected from an energy-source group including but not limited to a direct current source and an alternating current source.

4. The method of claim 3, wherein the alternating current source comprises:
    an alternating current source having frequency of substantially 62.5 kHz, or substantially 20.1 kHz, or substantially 57.1 kHz.

5. The method of claim 3, wherein the alternating current source comprises:
    an alternating current source having a frequency substantially between 1 kHz and 100 kHz.

6. The method of claim 1, wherein said measuring a patient parameter associated with a human body comprises:
    measuring a patient parameter selected from a patient-parameter group including but not limited to a resistance, a reactance, a combination of resistance and reactance, voltage, skin temperature, moisture, motion, color, optical properties, and pH.

7. The method of claim 1, wherein said locating the patient parameter on at least one curve associated with a defined prediction confidence level, where such curve correlates the patient parameter with a predicted maximum expected device parameter comprises:

selecting the at least one curve associated with a defined prediction confidence interval, where such curve correlates the patient parameter with a maximum expected device parameter, to be a curve whose associated prediction confidence level most closely matches a defined prediction confidence level.

8. The method of claim 7, wherein the associated prediction confidence level comprises:

a statistical inference of a variance of an empirically-generated data set which falls within a region baselined about a curve generated by a curve-fitting algorithm applied to the empirically generated data set.

9. The method of claim 8, wherein said statistical inference of a variance of an empirically-generated data set which falls within a region baselined about a curve generated by a curve-fitting algorithm applied to the empirically generated data set comprises:

a statistical inference of a variance of an empirically-generated data set which falls within a region baselined about a curve which has a relatively smallest error selected from the group including but not limited to least mean squares error and least absolute error relative to the empirically generated data set.

10. The method of claim 1, wherein said setting a limit on the energy source such that during defibrillation of a patient a defibrillation parameter associated with the maximum expected device parameter is within a defined tolerance comprises:

setting an upper limit on the energy source such that at least one defined electrical component is not damaged.

11. The method of claim 10, wherein said setting an upper limit on the energy source such that at least one defined electrical component is not damaged comprises:

setting a limit on the energy source such that during defibrillation of the patient a maximum expected defibrillation current is within a defined tolerance.

12. A method comprising:

measuring a patient parameter associated with a human body;

in response to the patient parameter, computing a maximum expected device parameter using a defibrillation source value calculated to provide a specified output defibrillation energy into a defibrillation-unit baseline impedance; and setting an upper limit on the defibrillation source such that the defibrillation parameter associated with the maximum expected device parameter does not exceed the absolute maximum rating of the at least one electrical component, if the computed maximum expected device parameter exceeds an absolute maximum rating of at least one electrical component.

13. The method of claim 12, wherein the defibrillation-unit baseline impedance comprises 50 ohms.

14. The method of claim 1, further comprising:

in response to the patient parameter, retrieving a minimum expected device parameter; and setting a limit on an energy source such that during defibrillation of the patient a defibrillation parameter associated with the minimum expected device parameter is within a defined tolerance.

15. The method of claim 14, wherein said setting a limit on an energy source such that during defibrillation a defibrillation parameter associated with the minimum expected device parameter is within a defined tolerance comprises:

setting a limit on the energy source such that during defibrillation a current is within a defined tolerance.

16. The method of claim 14, wherein said setting a limit on the energy source such that during defibrillation of a patient, a defibrillation parameter associated with the minimum expected device parameter is within a defined tolerance comprises:

setting a lower limit on the energy source such that the defibrillation parameter associated with the minimum expected device parameter exceeds a defibrillation threshold.

17. A method comprising:

measuring a patient parameter associated with a human body;

in response to the patient parameter retrieving a maximum expected device parameter;

in further response to the patient parameter, computing a minimum expected device parameter using a defibrillation source value calculated to provide a specified output defibrillation energy into a defibrillation-unit baseline impedance; and setting a lower limit on the defibrillation source such that the defibrillation parameter associated with the minimum expected device parameter is at or above the defibrillation threshold, if the computed minimum expected device parameter is less than the defined defibrillation threshold.

18. A system comprising:

circuitry for measuring a patient parameter associated with a human body;

circuitry for locating the patient parameter on at least one curve associated with a defined prediction confidence level, where such curve correlates the patient parameter with a predicted maximum expected device parameter;

circuitry for retrieving a predicted maximum expected device parameter from the at least one curve; and circuitry for setting a limit on an energy source such that during defibrillation of the patient a defibrillation parameter associated with the maximum expected device parameter is within a defined tolerance.

19. The system of claim 18, further comprising:

at least one electrical coupling adapted to form an electrical circuit with a human body, said at least one electrical coupling selected from a group including but not limited to a defibrillation electrode, an implantable electrode, a capacitive coupling electrical device, and a magnetic coupling electrical device.

20. The system of claim 18, further comprising:

at least one energy source adapted to energize the electrical circuit, said at least one energy source selected from selected from a group including but not limited to a direct current source and an alternating current source.

21. The system of claim 20, wherein the alternating current source comprises:

an alternating current source having frequency of substantially 62.5 kHz, or substantially 20.1 kHz, or substantially 57.1 kHz.

22. The system of claim 21, wherein the alternating current source comprises:
an alternating current source having a frequency substantially between 1 kHz and 100 kHz.

23. The system of claim 18, wherein said circuitry for measuring a patient parameter associated with a human body comprises:
circuitry for measuring a patient parameter selected from the group including but not limited to a resistance, a reactance, a combination of resistance and reactance, voltage, skin temperature, moisture, motion, color, optical properties, and pH.

24. The system of claim 18, wherein said circuitry for locating the patient parameter on at least one curve associated with a defined prediction confidence level, where such curve correlates the patient parameter with a predicted maximum expected device parameter comprises:
circuitry for selecting the at least one curve associated with a defined prediction confidence interval, where such curve correlates the patient parameter with a maximum expected device parameter, to be a curve whose associated prediction confidence level most closely matches a defined prediction confidence level.

25. The system of claim 24, wherein the associated prediction confidence level comprises:
a statistical inference of a variance of an empirically-generated data set which falls within a region baselined about a curve generated by a curve-fitting algorithm applied to the empirically generated data set.

26. The system of claim 25, wherein said statistical inference of a variance of an empirically-generated data set which falls within a region baselined about a curve generated by a curve-fitting algorithm applied to the empirically generated data set comprises:
a statistical inference of a variance of an empirically-generated data set which falls within a region baselined about a curve which has a relatively smallest error selected from the group including but not limited to least mean squares error and least absolute error relative to the empirically generated data set.

27. The system of claim 18, wherein said circuitry for setting a limit on the energy source such that during defibrillation of a patient a defibrillation parameter associated with the maximum expected device parameter is within a defined tolerance comprises:
circuitry for setting an upper limit such that at least one defined electrical component is not damaged.

28. The system of claim 26, wherein said circuitry for setting an upper limit such that at least one defined electrical component is not damaged comprises:
circuitry for setting a limit on the energy source such that during defibrillation of the patient a maximum expected defibrillation current is within a defined tolerance.

29. A system comprising:
circuitry for measuring a patient parameter associated with a human body;
circuitry, responsive to the patient parameter, for computing a maximum expected device parameter using a defibrillation source value calculated to provide a specified output defibrillation energy into a defibrillation-unit baseline impedance; and
circuitry for setting an upper limit on the defibrillation source such that the defibrillation parameter associated with the maximum expected device parameter does not exceed the absolute maximum rating of the at least one electrical component, if the computed maximum expected device parameter exceeds an absolute maximum rating of at least one electrical component.

30. The system of claim 29, wherein the defibrillation-unit baseline impedance comprises 50 ohms.

31. The system of claim 18, further comprising:
circuitry, responsive to the patient parameter, for retrieving a minimum expected device parameter; and
circuitry for setting a limit on an energy source such that during defibrillation of the patient a defibrillation parameter associated with the minimum expected device parameter is within a defined tolerance.

32. The system of claim 31, wherein said circuitry for setting a limit on an energy source such that during defibrillation a defibrillation parameter associated with the minimum expected device parameter is within a defined tolerance comprises:
circuitry for setting a limit on the energy source such that during defibrillation a current is within a defined tolerance.

33. The system of claim 31, wherein said circuitry for setting a limit on the energy source such that during defibrillation of a patient, a defibrillation parameter associated with the minimum expected device parameter is within a defined tolerance comprises:
circuitry for setting a lower limit on the energy source such that the defibrillation parameter associated with the minimum expected device parameter exceeds a defibrillation threshold.

34. A system comprising:
circuitry for measuring a patient parameter associated with a human body;
circuitry, responsive to the patient parameter, for retrieving a maximum expected device parameter;
circuitry, responsive to the patient parameter, for computing a minimum expected device parameter using a defibrillation source value calculated to provide a specified output defibrillation energy into a defibrillation-unit baseline impedance; and
circuitry for setting a lower limit on the defibrillation source such that the defibrillation parameter associated with the minimum expected device parameter is at or above the defibrillation threshold, if the computed minimum expected device parameter is less than the defined defibrillation threshold.

* * * * *

UNITED STATES PATENT AND TRADEMARK OFFICE
CERTIFICATE OF CORRECTION

PATENT NO.    : 6,772,006 B2
DATED         : August 3, 2004
INVENTOR(S)   : Daniel W. Piraino et al.

It is certified that error appears in the above-identified patent and that said Letters Patent is hereby corrected as shown below:

Column 18,
Line 60, delete "selected from".

Signed and Sealed this

Fifth Day of October, 2004

JON W. DUDAS
*Director of the United States Patent and Trademark Office*